(12) United States Patent
Wang et al.

(10) Patent No.: US 6,825,398 B2
(45) Date of Patent: Nov. 30, 2004

(54) SEED SPECIFIC 7Sα PROMOTER FOR EXPRESSING GENES IN PLANTS

(75) Inventors: Qi Wang, St. Louis, MO (US); Patrice Dubois, Richmond Heights, MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 10/235,618

(22) Filed: Sep. 5, 2002

(65) Prior Publication Data

US 2003/0093828 A1 May 15, 2003

Related U.S. Application Data

(60) Provisional application No. 60/316,975, filed on Sep. 5, 2001.

(51) Int. Cl.[7] .................. C12N 15/09; C12N 15/82; A01H 5/00; A01H 5/01
(52) U.S. Cl. .................. 800/287; 800/278; 800/298; 800/295; 800/320; 800/317; 800/306; 800/312; 435/468; 435/320.1; 536/24.1
(58) Field of Search ................. 800/278, 287, 800/298, 295, 320, 317, 306, 312, 317.3, 320.1, 320.2, 320.3, 322, 286; 435/320.1, 468, 419; 536/24.1, 23.6, 24.5

(56) References Cited

U.S. PATENT DOCUMENTS

| | | | | |
|---|---|---|---|---|
| 5,215,912 A | * | 6/1993 | Hoffman | 435/240.4 |
| 5,384,253 A | | 1/1995 | Krzyzek et al. | 800/292 |
| 5,689,052 A | | 11/1997 | Brown et al. | 800/30 |
| 6,177,613 B1 | * | 1/2001 | Coughlan et al. | 800/287 |
| 6,541,259 B1 | * | 4/2003 | Lassner et al. | 435/468 |

FOREIGN PATENT DOCUMENTS

| | | | |
|---|---|---|---|
| WO | WO 93/19190 | * | 9/1993 |
| WO | WO 00/10380 | * | 3/2000 |
| WO | WO 02/00899 A2 | | 6/2000 |

OTHER PUBLICATIONS

Kim et al. Plant Molecular Biology, vol. 24, pp. 105–117, 1994.*
Xia et al. J. Gen Microbiol 138:1309–1316, 1992.*
Lois et al. PNAS (USA), 95(5):2105–2110, 1998.*
Takahashi et al. PNAS (USA) 95(17):9879–9884, 1998.*
Manning et al. PNAS (USA) 96(21):11928–11933, 1999.*
Barley and Skolnick. Plant Physiology, 117:1317–1323, 1998.*
Shintani et al. Science 282 (5396): 2098–2100, 1998.*
P.R. Shewry et al.; *Seed Storage Proteins: Structures and Biosynthesis;* The Plant Cell; 7:945–946 (1995).
J.J.Doyle et al.; *The Glycosylated Seed Storage Proteins of Glycine max and Phaseolus vulgaris. Structural Homologies of Genes and Proteins,* J. Biol Chem.; 261(20):9228–9238: Jul. 15, 1986.
M.A.Schuler et al., *Structural Sequences are Conserved in the Genes Coding for the Alpha, Alpha' and Beta–Subunits of the Soybean 7S Seed Storage Protein;* Nucleic Acids Res.; 10(24):8245–8246; Dec. 20, 1982.
M.A.Schuler et al., *Closely Related Families of Genes Code for the Alpha and Alpha' Subunits of the Soybean 7S Storage Protein Complex;* Nucleic Acids Res.; 10(24):8225–8244; Dec. 20, 1982.

* cited by examiner

*Primary Examiner*—Medina A. Ibrahim
(74) *Attorney, Agent, or Firm*—Renessen LLC

(57) ABSTRACT

This invention provides promoters capable of transcribing heterologous nucleic acid sequences in seeds, and methods of modifying, producing, and using the same.

18 Claims, 11 Drawing Sheets

Top: M13759 Soybean mRNA for the alpha' subunit of beta-conglycinin [SEQ ID NO: 15]
Bottom: X17698 Soybean mRNA for the alpha subunit of beta-conglycinin[SEQ ID NO: 16]

```
 951 TTAAGATATACTATGATGAGAGCGCGGTTCCCATTACTGTTGCTGGGAGT 1000
               ||||||||||| |||||||||||||||||||||||| |
   1 ...........ATGATGAGAGCACGGTTCCCATTACTGTTGCTGGGACT 38

1001 TGTTTTCCTAGCATCAGTTTCTGTCTCATTTGGCATTGCGTATTGGGAAA 1050
     |||||||||  || |||||||||||||||||||||||||||  |||||||
  39 TGTTTTCCTGGCTTCAGTTTCTGTCTCATTTGGCATTGCTTACTGGGAAA 88

1051 AGCAGAACCCCAGTCACAACAAGTGCCTCCGAAGTTGCAATAGCGAGAAA 1100
     |  |||||||||  ||||||||||| |||| ||||||||||||||||| |
  89 AAGAGAACCCCAAACACAACAAGTGTCTCCAGAGTTGCAATAGCGAGAGA 138

1101 GACTCCTACAGGAACCAAGCATGCCACGCTCGTTGCAACCTCCTTAAGGT 1150
     ||||| ||||||||||||||||||||||||||||||||||||||||||||
 139 GACTCGTACAGGAACCAAGCATGCCACGCTCGTTGCAACCTCCTTAAGGT 188

1151 GGAGGAAGAAGAA...GAATGCGAAGAAGGTCAAATTCCACGACCACGAC 1197
     |||| ||||||||   |||  |  ||| || |  ||||||||||||||||
 189 GGAGAAAGAAGAATGTGAAGAAGGTGAAATTCCACGACCACGACCACGAC 238

1198 CACAACACCCGGAGAGGGAACGTCAGCAACACGGTGAGAAGGAGGAAGAC 1247
     |||||||||||||||||||||| |||||||  ||||||||||||||||||
 239 CACAACACCCGGAGAGGGAACCTCAGCAACCCGGTGAGAAGGAGGAAGAC 288

1248 GAAGGTGAGCAGCCACGTCCATTCCCATTCCCACGCCCACGCCAACCTCA 1297
     |||| ||||||| ||||||||||  ||||||||||||||   ||||||| 
 289 GAAGATGAGCAACCACGTCCAATCCCATTCCCACGCCCA...CAACCTCG 335

1298 TCAAGAGGAAGAGCACGAGCAGAAGGAGGAACACGAATGGCATCGCAAGG 1347
     ||||| |||||||||||||||||| |||||| ||||||| |||||||||
 336 TCAAGAAGAAGAGCACGAGCAGAGAGAGGAACAGGAATGGCCTCGCAAGG 385

1348 AGGAAAAACACGGAGGAAAGGGAAGTGAAGAGGAACAAGATGAACGTGAA 1397
     |||||||| |||| ||||||||||||||||||||||  ||  |
 386 AGGAAAAACGCGGAGAAAAGGGAAGTGAAGAGGAAGATGAGG........ 427

1398 CACCCACGCCCACACCAACCTCATCAAAAGGAAGAGGAAAAGCACGAATG 1447
                         |  ||||  ||||| |  | ||| |
 428 ......................ATGAGGATGAGGAACAAGATGAACG 452

1448 GCAACACAAGCAGGAAAAGCACCAAGGAAAGGAAAGTGAAGAAGAAGAAG 1497
     ||| |   |        ||| |   |   |  | |||||  | | |
 453 TCAATTC...CCATTCCCACGCCCACCTCATCAGAAGGAAGAGCGAAACG 499
```

Figure 1. Alignment of two 7S alpha cDNA sequences

```
P-Gm-7Salpha-1T.seq  Length: 1724  5-Jul-01  11:16:17  Check: 7862

1 AAGCTTCTGC AGGGTCGACG GCCCGGGCTG GTCTGTCTTT TCAATTTTTT
  51 TGGCCACATA TTATTCGGGT TCTGTGACCT TTTCAAAATG ACTGCTATTA
 101 CCTCCTGACC TTGCTATTAC ATCTTGACCA TCACTAGGCA TTTAAAAGTA
 151 TTAGTCATAG TCACATATTA CTACAAAGCG AGATTGATCT CTCTAATCTA
 201 ATGGGTGGGA AAACACTTAT AATATATGAT TCAAGAAAAG AAAGTAAATA
 251 AAACAATTTT ATTATATAAA GACTATTAGG ATAAAAAAAA CCTTAAAAGT
 301 GCTTGGATTT GGACCAGACT TGAATTTTAA TTTAATGATA TTATAATATG
 351 TGAATATATT TTTGAGACAA TTGTAAATTT CAGATAAAAA AATAATGTAA
 401 TTAAAATTGT AATAACTATA TCGTATACTT AATTAATTAT TAAATGTGAC
 451 AAAAAAGATA TACATCAAAA CTTAATGTTT CATGACTTTT TTTTTTAATG
 501 TGTGTCCTAA ATAGAAATTA AAAATAAAAA TTATTATATC CAAATGAAAA
 551 AAACATTTAA TACGTATTAT TTAAGAAATA ACAATATATT TATATTTTAA
 601 TATGTATTCA CATGTAAATT TAAAAACAAA AACAAAATTT CTCTTTTATT
 651 GATTAATTAA AATAATTTTA TAACTACATT TATTTCTAT TATTATCAAT
 701 TTTCTTCTGT TTTTTTATTT GGCATATATA CCTAGACAAG TCAAAAAATG
 751 ACTATTCTTT AATAATCAAT CATTATTCTT ACATATTGTT CGAACTACGA
 801 GTTATGAAGT GTCAATTGCA CCTTAGTGTT TTGATAGGCC TCCATTTGCC
 851 GCTCATTAAT TAATTTGATA ACAGCCGTAC CGATCAATTA CTTATGCTTC
 901 TTCCATCGTA ATTATATGCA TGTCGGTTCT TTTAATCTTG GTACTCTCGA
 951 ATGCCACCAC AACACTGACT AGTCTCTTGG ATCATGAGAA AAAGCCAAAG
1001 AACAAAAAG ACAACATAAA GAGTATCCTT TGCAAAAAAA TGTCTAAGTT
1051 CATAAAATAC AAACAAAAC GCAATCACAC ACAGTGGACC CAAAAGCCAT
1101 GCACAACAAC ACGTACTCAC CAAGGTGCAA TCGTGCTGCC CAAAAACATT
1151 CACCAACTCA ATCCATGATG AGCCCACACA TTTGTTGTTT GTAACCAAAT
1201 CTCAAACGCG GTGTTCTCTT TGGAAAGCAA CCATATCAGC ATATCACACT
1251 ATCTAGTCTC TTGGATCATG CATGCGCAAC CAAAAGACAA CACATAAAGT
1301 ATCCTTTCGA AAGCAATGTC CAAGTCCATC AAATAAAATT GAGACAAAAT
1351 GCAACCTCAC CCCACTTCAC TATCCATGGC TGATCAAGAT CGCCGCGTCC
1401 ATGTAGGTCT AAATGCCATG CACATCAACA CGTACTCAAC ATGCAGCCCA
1451 AATTGCTCAC CATCGCTCAA CACATTTCTT GTTAATTTCT AAGTACACTG
1501 CCTATGCGAC TCTAACTCGA TCACAACCAT CTTCCGTCAC ATCAATTTTG
1551 TTCAATTCAA CACCCGTCAA CTTGCATGCC ACCCCATGCA TGCAAGTTAA
1601 CAAGAGCTAT ATCTCTTCTA TGACTATAAA TACCCGCAAT CTCGGTCCAG
1651 GTTTTCATCA TCGAGAACTA GTTCAATATC CTAGTATACC TTAATAAATA
1701 ATTTAAGATA CTAGATCTCC ATGG
```

Figure 2a. Sequence of p-GEM-T 1T

[SEQ ID NO: 12]

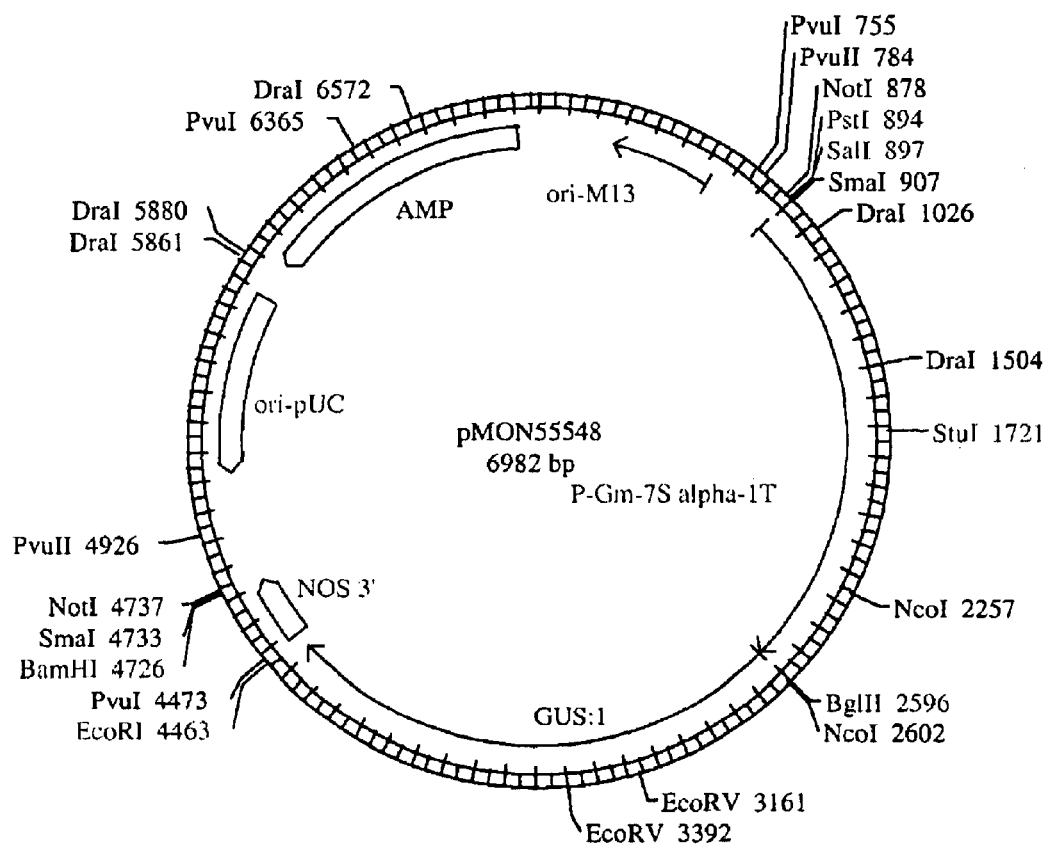
Figure 2b. A plasmid map of pMON55548

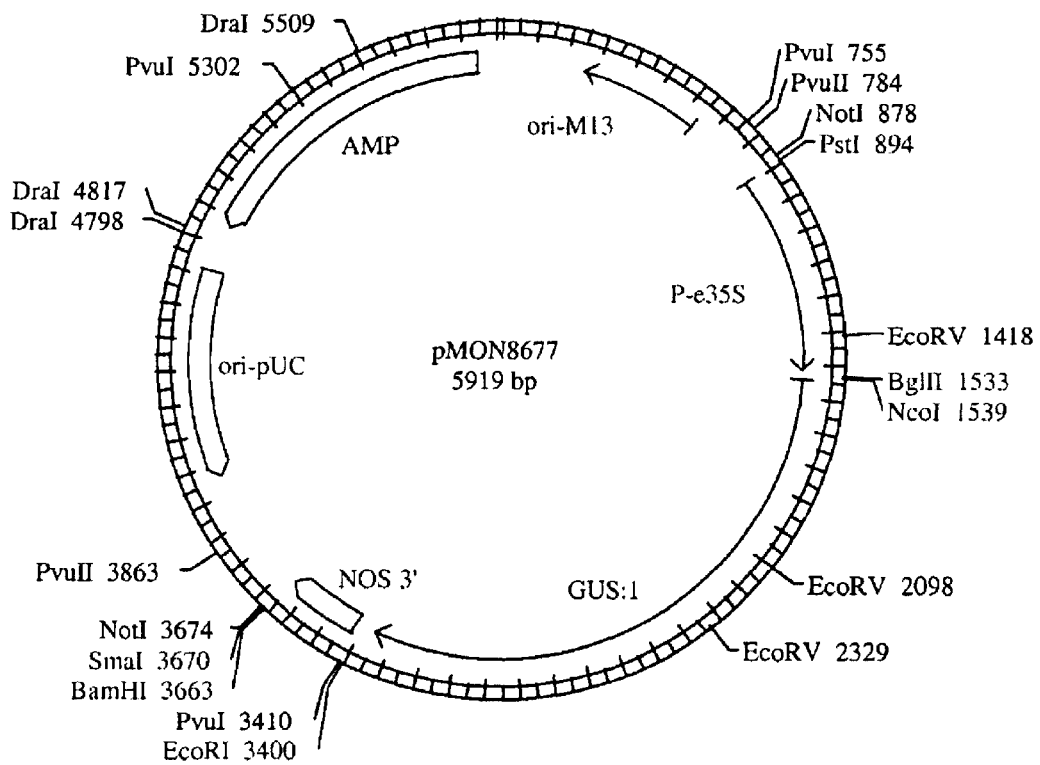
Figure 3a. A Plasmid Map of pMON8677

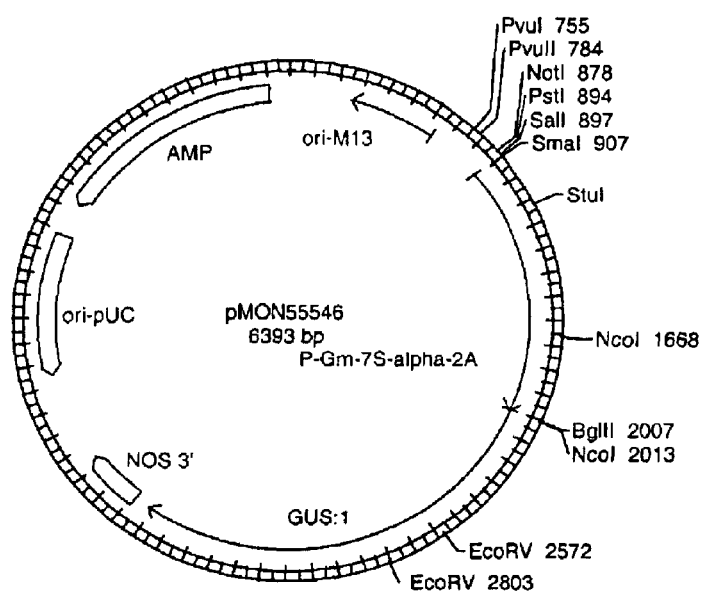
Figure 3b. Plasmid map for vector pMON55546

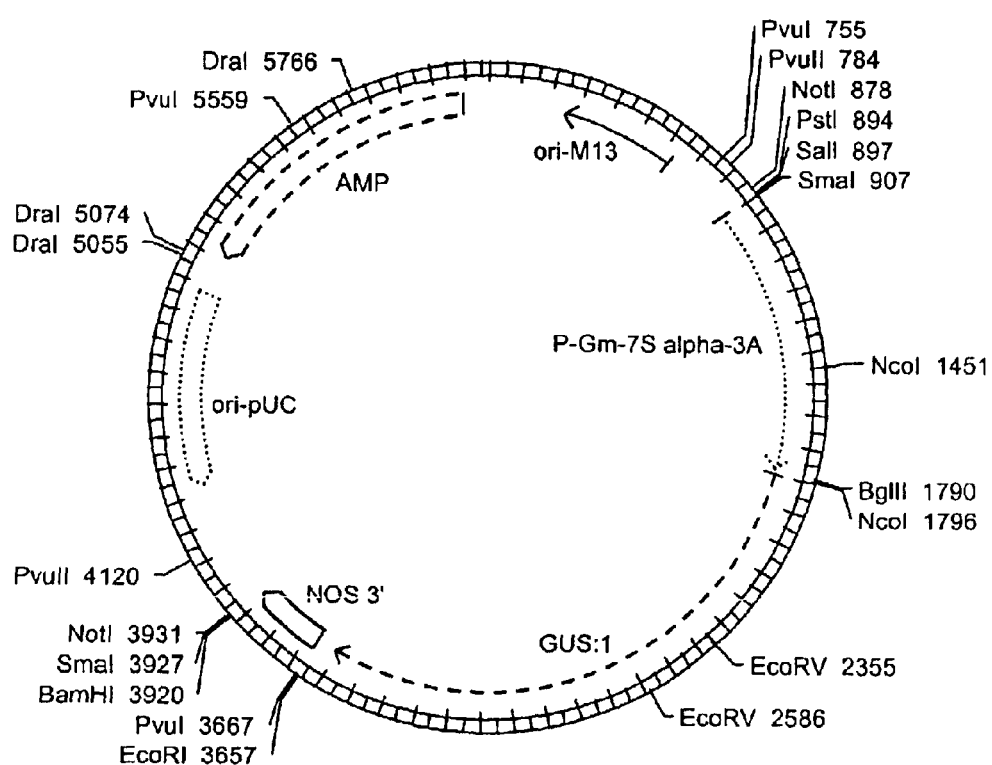
Figure 4. Plasmid map for vector pMON55547

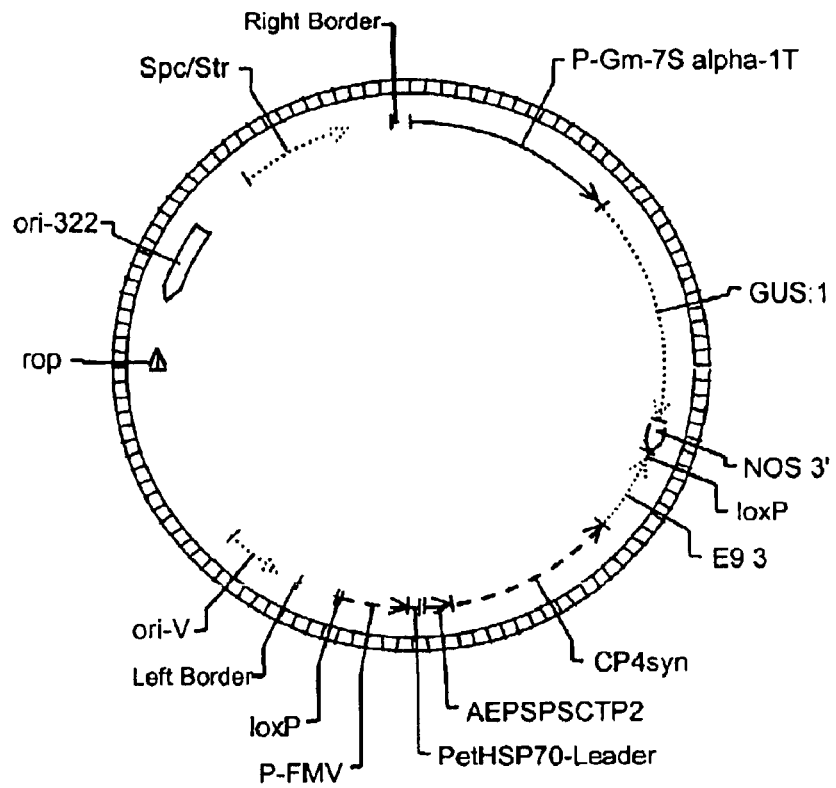
Figure 5. A plasmid map of pMON55554

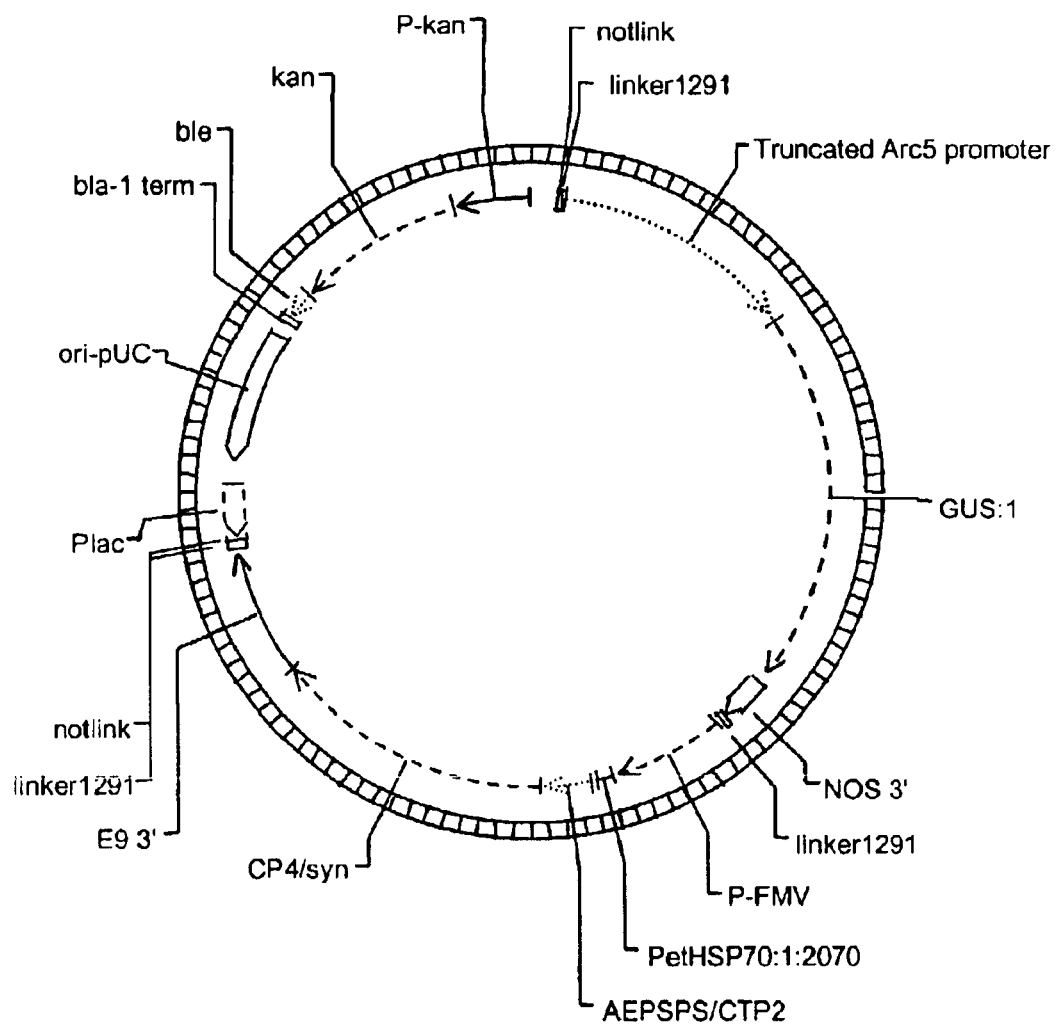
Figure 6. A plasmid map of pMON55542

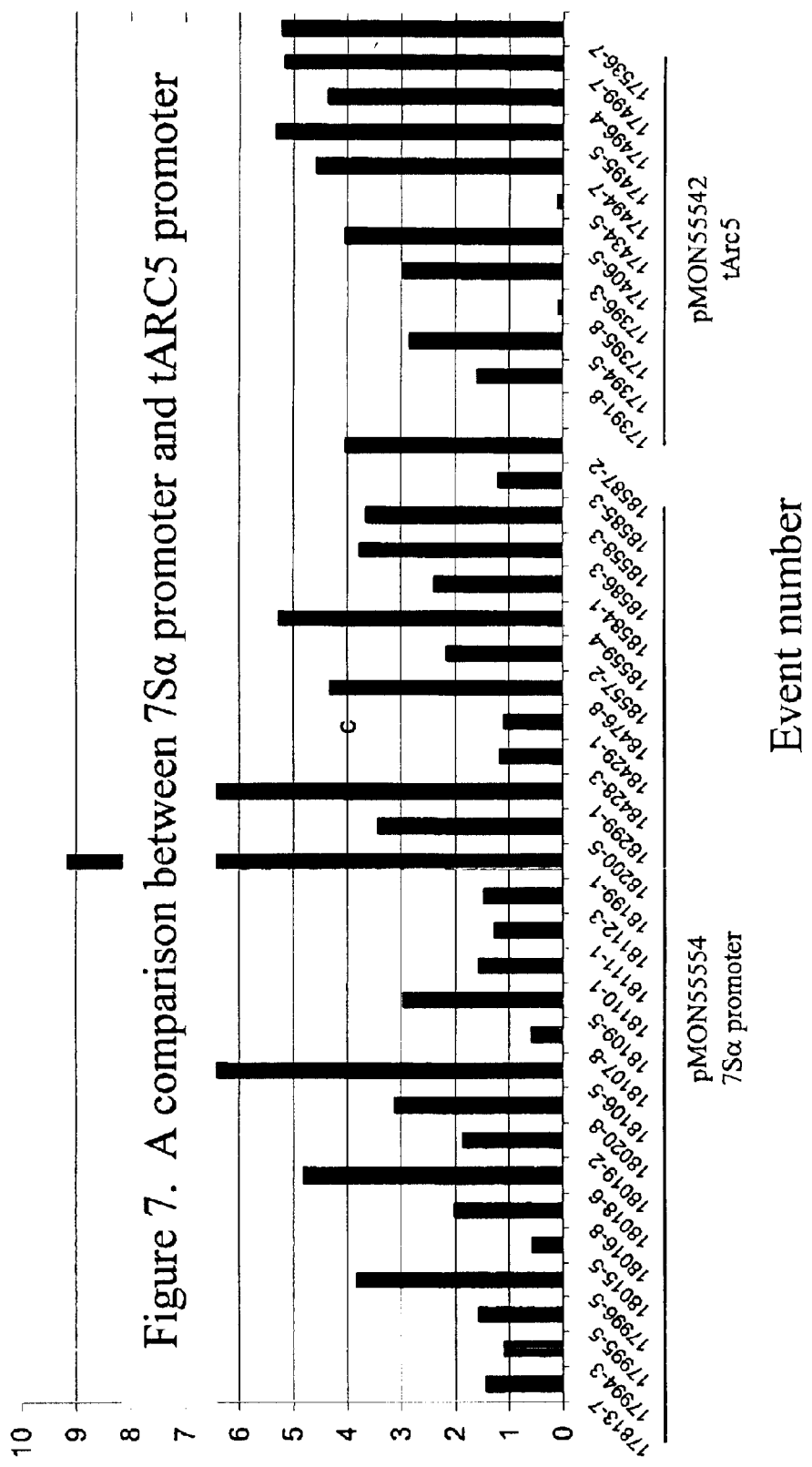
Figure 7. A comparison between 7Sα promoter and tARC5 promoter

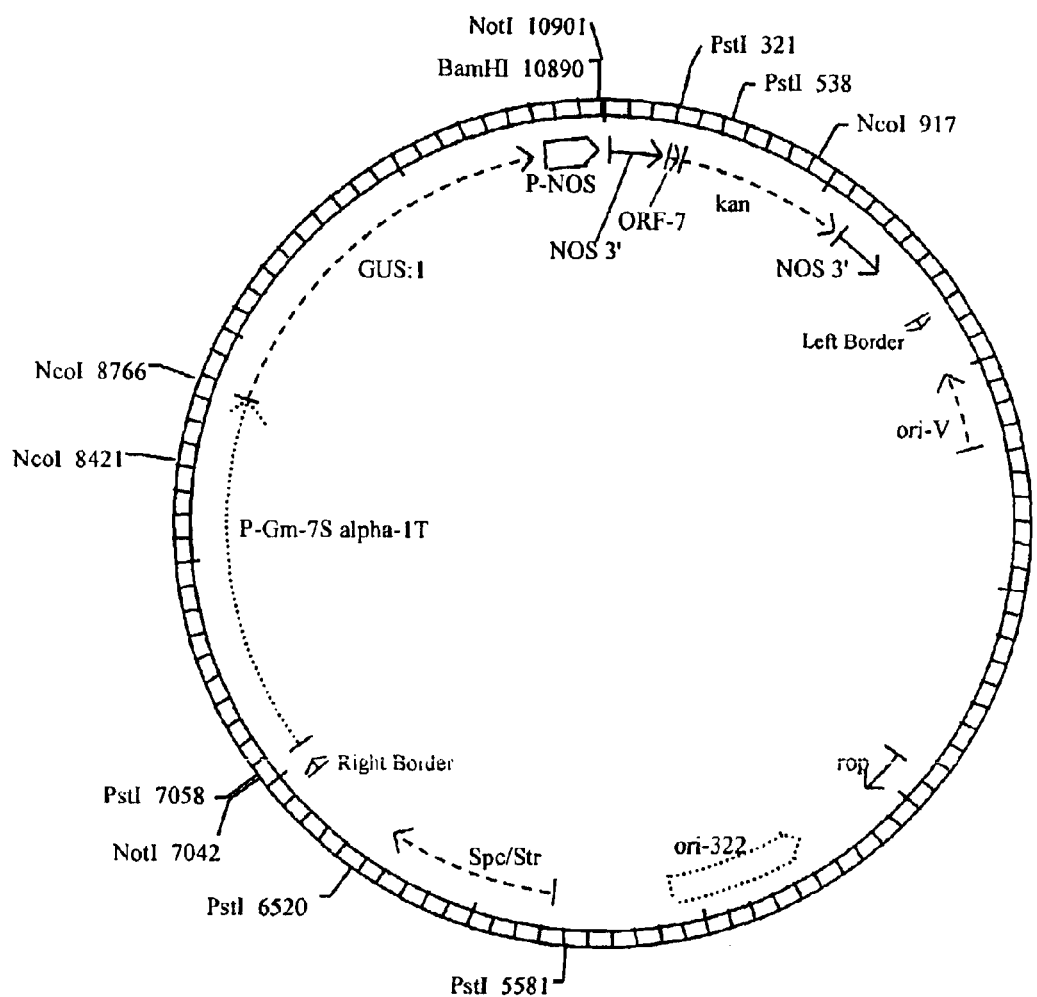
Figure 8. A plasmid map of pMON55553

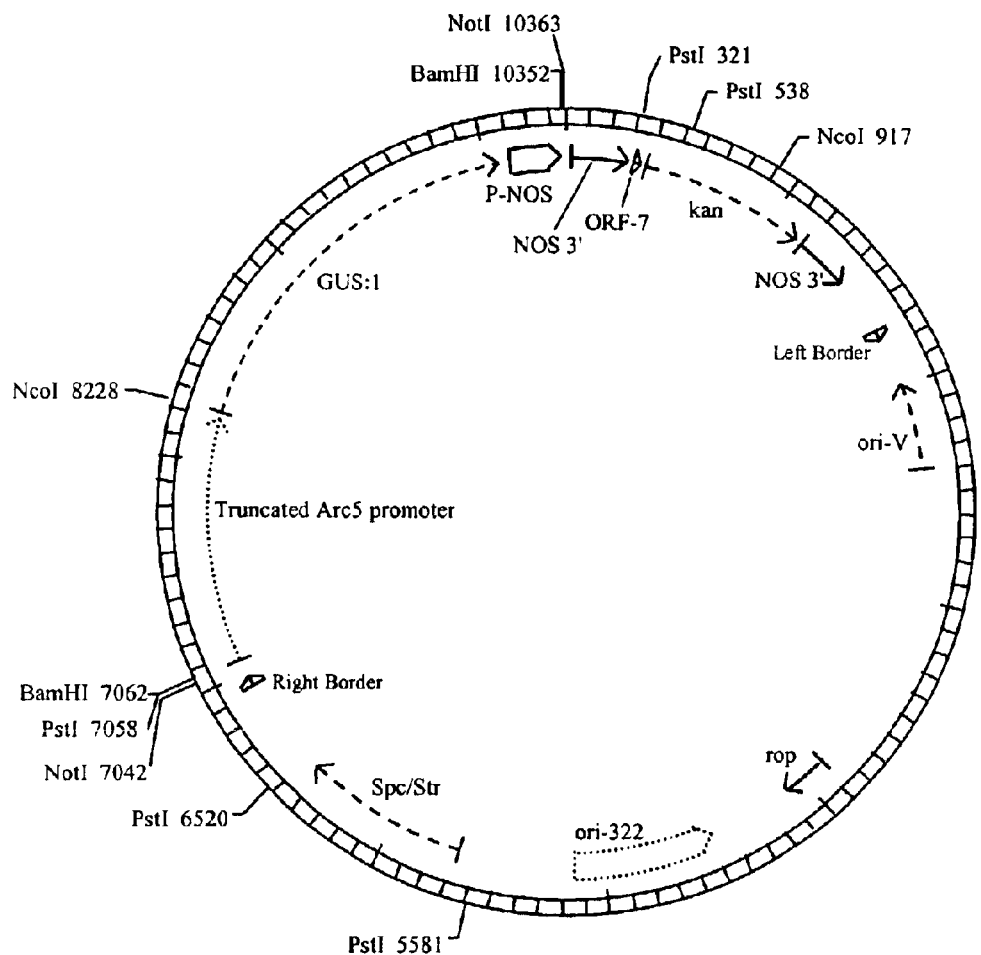
Figure 9. A plasmid map of pMON55541

SEQUENCE LISTING

<160> NUMBER OF SEQ ID NOS: 16

<210> SEQ ID NO 1
<211> LENGTH: 1318
<212> TYPE: DNA
<213> ORGANISM: Glycine max

<400> SEQUENCE: 1

```
aagcttctgc agggtcgacg gcccgggctg gtaaaaacaa aaacaaaatt tctcttttat      60
tgattaatta aaataatttt ataactacat ttattttcta ttattatcaa ttttcttctg     120
tttttttatt tggcatatat acctagacaa gtcaaaaaat gactattctt taataatcaa     180
tcattattct tacatattgt tcgaactacg agttatgaag tgtcaattgc accttagtgt     240
tttgataggc ctccatttgc cgctcattaa ttaatttgat aacagccgta ccgatcaatt     300
acttatgctt cttccatcgt aattatatgc atgtcggttc ttttaatctt ggtactctcg     360
aatgccacca caacactgac tagtctcttg gatcatgaga aaaagccaaa gaacaaaaaa     420
gacaacataa agagtatcct tgcaaaaaa atgtctaagt tcataaaata caaacaaaaa     480
cgcaatcaca cacagtggac ccaaaagcca tgcacaacaa cgcgtactca ccaaggtgca     540
atcgtgctgc ccaaaaacat tcaccaactc aatccatgat gagcccacac atttgttgtt     600
tgtaaccaaa tctcaaacgc ggtgttctct ttggaaagca accatatcag catatcacac     660
tatctagtct cttggatcac gcatgcgcaa ccaaaagaca acacataaag tatcctttcg     720
aaagcaatgt ccaagtccat caaataaaat tgagacaaaa tgcaacctca ccccacttca     780
ctatccatgg ctgatcaaga tcgccgcgtc catgtaggtc taaatgccat gcacatcaac     840
acgtactcaa catgcagccc aaattgctca ccatcgctca acacatttct tgttaatttc     900
taagtacact gcctatgcga ctctaactcg atcacaacca tcttccgtca catcaatttt     960
gttcaattca acacccgtca acttgcatgc cacccccatgc atgcaagtta acaagagcta    1020
tatctcttct atgactataa atgcccgcaa tctcggtcca ggttttcatc atcgagaact    1080
agttcaatat cctagtatac cttaataaat aatttaagat actatgatga gagcacggtt    1140
cccattactg ttgctgggac ttgttttcct ggcttcagtt tctgtctcat ttggcattgc    1200
ttactgggaa aaagagaacc ccaaacacaa caagtgtctc cagagttgca atagcgagag    1260
agactcgtac aggaaccaag catgccacgc tcgttgcaac ctccttagat ctccatgg      1318
```

<210> SEQ ID NO 2
<211> LENGTH: 1724
<212> TYPE: DNA
<213> ORGANISM: Glycine max

<400> SEQUENCE: 2

```
aagcttctgc agggtcgacg gcccgggctg gtctgtcttt tcaatttttt tggccacata      60
ttattcgggt tctgtgacct tttcaaaatg actgctatta cctcctgacc ttgctattac     120
atcttgacca tcactaggca tttaaaagta ttagtcatag tcacatatta ctacaaagcg     180
agattgatct ctctaatcta atgggtggga aaacacttat aatatatgat tcaagaaaag     240
aaagtaaata aaacaatttt attatataaa gactattagg ataaaaaaaa ccttaaaagt     300
gcttggattt ggaccagact tgaattttaa tttaatgata ttataatatg tgaatatatt     360
tttgagacaa ttgtaaattt cagataaaaa aataatgtaa ttaaaattgt aataactata     420
tcgtatacct aattaattat taaatgtgac aaaaaagata tacatcaaaa cttaatgttt     480
```

```
catgactttt ttttttaatg tgtgtcctaa atagaaatta aaaataaaaa ttattatatc     540
caaatgaaaa aaacatttaa tacgtattat ttaagaaata acaatatatt tatattttaa     600
tatgtattca catgtaaatt taaaaacaaa acaaaattt ctcttttatt gattaattaa      660
ataattttta taactacatt tattttctat tattatcaat tttcttctgt ttttttattt     720
ggcatatata cctagacaag tcaaaaaatg actattcttt aataatcaat cattattctc     780
acatattgtt cgaactacga gttagtaagt gtcaattgca ccttagtgtt ttgataggcc     840
tccatttgcc gctcattaat taatttgata acagccgtac cgatcaatta cttatgcttc     900
ttccatcgta attatatgca tgtcggttct tttaatcttg gtactctcga atgccaccac     960
aacactgact agtctcttgg atcatgagaa aaagccaaag aacaaaaaag acaacataaa    1020
gagtatcctt tgcaaaaaaa tgtctaagtt cataaaatac aaacaaaaac gcaatcacac    1080
acagtggacc caaaagccat gcacaacaac acgtactcac caaggtgcaa tcgtgctgcc    1140 caaaacatt caccaactca atccatgatg agcccacaca tttgttgttt gtaaccaaat     1200 ctaaacgcg tgttctctt tggaaagcaa ccatatcagc atatcacact atctagtctc      1260
ttggatcatg catgcgcaac caaaagacaa cacataaagt atcctttcga aagcaatgtc    1320
caagtccatc aaataaaatt gagacaaaat gcaacctcac cccacttcac tatccatggc    1380
tgatcaagat cgccgcgtcc atgtaggtct aaatgccatg cacatcaaca cgtactcaac    1440
atgcagccca aattgctcac catcgctcaa cacatttctt gttaatttct aagtacactg    1500
cctatgcgac tctaactcga tcacaaccat cttccgtcac atcaattttg ttcaattcaa    1560
cacccgtcaa cttgcatgcc accccatgca tgcaagttaa caagagctat atctcttcta    1620
tgactataaa tacccgcaat ctcggtccag gttttcatca tcgagaacta gttcaatatc    1680
ctagtatacc ttaataaata atttaagata ctagatctcc atgg                    1724
```

<210> SEQ ID NO 3
<211> LENGTH: 1135
<212> TYPE: DNA
<213> ORGANISM: Glycine max

<400> SEQUENCE: 3

```
aagcttctgc agggtcgacg gcccgggctg gtaaaaacaa aaacaaaatt tctcttttat      60
tgattaatta aaataatttt ataactacat ttattttcta ttattatcaa ttttcttctg    120
ttttttattt tggcatatat acctagacaa gtcaaaaaat gactattctt taataatcaa    180
tcattattct tacatattgt tcgaactacg agttatgaag tgtcaattgc accttagtgt    240
tttgataggc ctccatttgc cgctcattaa ttaatttgat aacagccgta ccgatcaatt    300
cattatgctt cttccatcgt aattatatgc atgtcggttc ttttaatctt ggtactctca    360
aatgccacca caacactgac tagtctcttg gatcatgaga aaaagccaaa gaacaaaaaa    420
gacaacataa agagtatcct ttgcaaaaaa atgtctaagt tcataaaata caaacaaaaa    480
cgcaatcaca cacagtggac ccaaaagcca tgcacaacaa cgcgtactca ccaaggtgca    540
atcgtgctgc ccaaaaacat tcaccaactc aatccatgat gagcccacac atttgttgtt    600
tgtaaccaaa tctcaaacgc ggtgttctct ttggaaagca accatatcag catatcacac    660
tatctagtct cttggatcac gcatgcgcaa ccaaaagaca acacataaag tatcctttcg    720
aaagcaatgt ccaagtccat caaataaaat tgagacaaaa tgcaacctca ccccacttca    780
ctatccatgg ctgatcaaga tcgccgcgtc catgtaggtc taaatgccat gcacatcaac    840
```

```
acgtactcaa catgcagccc aaattgctca ccatcgctca acacatttct tgttaatttc      900
taagtacact gcctatgcga ctctaactcg atcacaacca tcttccgtca catcaatttt      960
gttcaattca acaccgtca acttgcatgc caccccatgc atgcaagtta acaagagcta     1020
tatctcttct atgactataa atgcccgcaa tctcggtcca ggttttcatc atcgagaact    1080
agttcaatat cctagtatac cttaataaat aatttaagat actagatctc catgg         1135
```

<210> SEQ ID NO 4
<211> LENGTH: 918
<212> TYPE: DNA
<213> ORGANISM: Glycine max

<400> SEQUENCE: 4

```
aagcttctgc agggtcgacg gcccgggctg gtcctccatt tgccgctcat taattaattt       60
gataacagcc gtaccgatca attacttatg cttcttccat cgtaattata tgcatgtcgg      120
ttctttttaat cttggtactc tcgaatgcca ccacaacact gactagtctc ttggatcatg     180
agaaaaagcc aaagaacaaa aaagacaaca taaagagtat cctttgcaaa aaaatgtcta      240
agttcataaa atacaaacaa aaacgcaatc acacacagtg gacccaaaag ccatgcacaa      300
caacacgtac tcaccaaggt gcaatcgtgc tgcccaaaaa cattcaccaa ctcaatccat      360
gatgagccca cacatttgtt gtttgtaacc aaatctcaaa cgcggtgttc tctttggaaa     420
gcaaccatat cagcatatca cactatctag tctcttggat catgcatgcg caaccaaaag      480
acaacacata aagtatcctt tcgaaagcaa tgtccaagtc catcaaataa aattgagaca      540
aaatgcaacc tcaccccact tcactatcca tggctgatca agatcgccgc gtccatgtag      600
gtctaaatgc catgcacatc aacacgtact caacatgcag cccaaattgc tcaccatcgc      660
tcaacacatt tcttgttaat ttctaagtac actgcctatg cgactctaac tcgatcacaa      720
ccatcttccg tcatcaat tttgttcaat tcaacacccg tcaacttgca tgccacccca      780
tgcatgcaag ttaacaagag ctatatctct tctatgacta taaatacccg caatctcggt      840
ccaggttttc atcatcgaga actagttcaa tatcctagta taccttaata ataatttaa      900
gatactagat ctccatgg                                                    918
```

<210> SEQ ID NO 5
<211> LENGTH: 32
<212> TYPE: DNA
<213> ORGANISM: Artificial
<220> FEATURE:
<223> OTHER INFORMATION: primer sequence

<400> SEQUENCE: 5

```
aagcttctgc agggtcgacg gcccgggctg gt                                     32
```

<210> SEQ ID NO 6
<211> LENGTH: 30
<212> TYPE: DNA
<213> ORGANISM: Artificial
<220> FEATURE:
<223> OTHER INFORMATION: primer sequence

<400> SEQUENCE: 6

```
cttctgatga ggtgggcgtg ggaatgggaa                                        30
```

<210> SEQ ID NO 7
<211> LENGTH: 30
<212> TYPE: DNA
<213> ORGANISM: Artificial

```
<220> FEATURE:
<223> OTHER INFORMATION: primer sequence

<400> SEQUENCE: 7
cttctgatga ggtgggcgtg ggaatgggaa                                        30

<210> SEQ ID NO 8
<211> LENGTH: 38
<212> TYPE: DNA
<213> ORGANISM: Artificial
<220> FEATURE:
<223> OTHER INFORMATION: primer sequence

<400> SEQUENCE: 8
ccatggagat ctagtatctt aattatttat taaggtat                              38

<210> SEQ ID NO 9
<211> LENGTH: 21
<212> TYPE: DNA
<213> ORGANISM: Artificial
<220> FEATURE:
<223> OTHER INFORMATION: primer sequence

<400> SEQUENCE: 9
gtatacgact cactataggg c                                                21

<210> SEQ ID NO 10
<211> LENGTH: 37
<212> TYPE: DNA
<213> ORGANISM: Artificial
<220> FEATURE:
<223> OTHER INFORMATION: primer sequences

<400> SEQUENCE: 10
ccatggagat ctaaggaggt tgcaacgagc gtggcat                               37

<210> SEQ ID NO 11
<211> LENGTH: 1318
<212> TYPE: DNA
<213> ORGANISM: Glycine max

<400> SEQUENCE: 11
aagcttctgc agggtcgacg gcccgggctg gtaaaaacaa aaacaaaatt tctcttttat       60
tgattaatta aaataatttt ataactacat ttattttcta ttattatcaa ttttcttctg      120 ttttttttatt tggcatatat acctagacaa gtcaaaaaat gactattctt taataatcaa     180
tcattattct tacatattgt tcgaactacg agttatgaag tgtcaattgc accttagtgt      240
tttgataggc ctcccatttgc cgctcattaa ttaatttgat aacagccgta ccgatcaatt     300
acttatgctt cttccatcgt aattatatgc atgtcggttc ttttaatctt ggtactctcg      360
aatgccacca caaacactgac tagtctcttg gatcatgaga aaaagccaaa gaacaaaaaa     420
gacaacataa agagtatcct ttgcaaaaaa atgtctaagt tcataaaata caaacaaaaa      480
cgcaatcaca cacagtggac ccaaaagcca tgcacaacaa cacgtactca ccaaggtgca     540
atcgtgctgc ccaaaaacat tcaccaactc aatccatgat gagcccacac atttgttgtt     600
tgtaaccaaa tctcaaacgc ggtgttctct ttggaaagca accatatcag catatcacac     660
tatctagtct cttggatcat gcatgcgcaa ccaaaagaca acacataaag tatcctttcg      720
aaagcaatgt ccaagtccat caaataaaat tgagacaaaa tgcaacctca ccccacttca     780
ctatccatgg ctgatcaaga tcgccgcgtc catgtaggtc taaatgccat gcacatcaac     840
```

-continued

```
acgtactcaa catgcagccc aaattgctca ccatcgctca acacatttct tgttaatttc      900
taagtacact gcctatgcga ctctaactcg atcacaacca tcttccgtca catcaatttt      960
gttcaattca acaccgtca acttgcatgc accccatgc atgcaagtta acaagagcta       1020
tatctcttct atgactataa atacccgcaa tctcggtcca ggttttcatc atcgagaact     1080
agttcaatat cctagtatac cttaataaat aatttaagat actatgatga gagcacggtt     1140
cccattactg ttgctgggac ttgttttcct ggcttcagtt tctgtctcat ttggcattgc     1200
ttactgggaa aaagagaacc ccaaacacaa caagtgtctc cagagttgca atagcgagag     1260
agactcgtac aggaaccaag catgccacgc tcgttgcaac ctccttagat ctccatgg      1318
```

<210> SEQ ID NO 12
<211> LENGTH: 1724
<212> TYPE: DNA
<213> ORGANISM: Glycine max

<400> SEQUENCE: 12

```
aagcttctgc agggtcgacg gcccgggctg gtctgtcttt tcaattttt tggccacata       60 ttattcgggt tctgtgacct tttcaaaatg actgctatta cctcctgacc ttgctattac      120
atcttgacca tcactaggca tttaaaagta ttagtcatag tcacatatta ctacaaagcg      180
agattgatct ctctaatcta atgggtggga aaacacttat aatatatgat tcaagaaaag      240
aaagtaaata aaacaatttt attatataaa gactattagg ataaaaaaa ccttaaaagt       300 gcttggattt ggaccagact tgaattttaa tttaatgata ttataatatg tgaatatatt      360
tttgagacaa ttgtaaattt cagataaaaa aataatgtaa ttaaaattgt aataactata      420
tcgtatactt aattaattat taaatgtgac aaaaaagata tacatcaaaa cttaatgttt      480
catgactttt ttttttaatg tgtgtcctaa atagaaatta aaaataaaaa ttattatatc      540
caaatgaaaa aaacatttaa tacgtattat ttaagaaata acaatatatt tatattttaa      600
tatgtattca catgtaaatt taaaaacaaa acaaaatttt ctcttttatt gattaattaa      660
aataatttta taactacatt tattttctat tattatcaat tttcttctgt ttttttattt      720
ggcatatata cctagacaag tcaaaaaatg actattcttt aataatcaat cattattctt      780
acatattgtt cgaactacga gttatgaagt gtcaattgca ccttagtgtt ttgataggcc      840
tccatttgcc gctcattaat taatttgata acagccgtac cgatcaatta cttatgcttc      900
ttccatcgta attatatgca tgtcggttct tttaatcttg gtactctcga atgccaccac      960
aacactgact agtctcttgg atcatgagaa aaagccaaag aacaaaaaag acaacataaa     1020
gagtatcctt tgcaaaaaaa tgtctaagtt cataaaatac aaacaaaaac gcaatcacac     1080
acagtggacc caaaagccat gcacaacaac acgtactcac caaggtgcaa tcgtgctgcc     1140
caaaaacatt caccaactca atccatgatg agcccacaca tttgttgttt gtaaccaaat     1200
ctcaaacgcg gtgttctctt tggaaagcaa ccatatcagc atatcacact atctagtctc     1260
ttggatcatg catgcgcaac caaaagacaa cacataaagt atcctttcga agcaatgtc      1320 caagtccatc aaataaaatt gagacaaaat gcaacctcac cccacttcac tatccatggc     1380
tgatcaagat cgccgcgtcc atgtaggtct aaatgccatg cacatcaaca cgtactcaac     1440
atgcagccca aattgctcac catcgctcaa cacatttctt gttaatttct aagtacactg     1500
cctatgcgac tctaactcga tcacaaccat cttccgtcac atcaattttg ttcaattcaa     1560
cacccgtcaa cttgcatgcc accccatgca tgcaagttaa caagagctat atctcttcta     1620
tgactataaa tacccgcaat ctcggtccag gttttcatca tcgagaacta gttcaatatc     1680
```

```
ctagtatacc ttaataaata atttaagata ctagatctcc atgg            1724

<210> SEQ ID NO 13
<211> LENGTH: 1135
<212> TYPE: DNA
<213> ORGANISM: Glycine max

<400> SEQUENCE: 13
aagcttctgc agggtcgacg gcccgggctg gtaaaaacaa aaacaaaatt tctcttttat    60
tgattaatta aaataatttt ataactacat ttattttcta ttattatcaa ttttcttctg   120
ttttttttatt tggcatatat acctagacaa gtcaaaaaat gactattctt taataatcaa   180
tcattattct tacatattgt tcgaactacg agttatgaag tgtcaattgc accttagtgt   240
tttgataggc ctccatttgc cgctcattaa ttaatttgat aacagccgta ccgatcaatt   300
acttatgctt cttccatcgt aattatatgc atgtcggttc ttttaatctt ggtactctcg   360
aatgccacca caacactgac tagtctcttg gatcatgaga aaaagccaaa gaacaaaaaa   420
gacaacataa agagtatcct ttgcaaaaaa atgtctaagt tcataaaata caaacaaaaa   480
cgcaatcaca cacagtggac ccaaaagcca tgcacaacaa cacgtactca ccaaggtgca   540
atcgtgctgc ccaaaaacat tcaccaactc aatccatgat gagcccacac atttgttgtt   600
tgtaaccaaa tctcaaacgc ggtgttctct ttggaaagca accatatcag catatcacac   660
tatctagtct cttggatcat gcatgcgcaa ccaaaagaca acacataaag tatccttttcg   720
aaagcaatgt ccaagtccat caaataaaat tgagacaaaa tgcaacctca ccccacttca   780
ctatccatgg ctgatcaaga tcgccgcgtc catgtaggtc taaatgccat gcacatcaac   840
acgtactcaa catgcagccc aaattgctca ccatcgctca acacatttct tgttaatttc   900
taagtacact gcctatgcga ctctaactcg atcacaacca tcttccgtca catcaatttt   960
gttcaattca acaccccgtca acttgcatgc caccccatgc atgcaagtta acaagagcta  1020
tatctcttct atgactataa atacccgcaa tctcggtcca ggttttcatc atcgagaact  1080
agttcaatat cctagtatac cttaataaat aatttaagat actagatctc catgg        1135

<210> SEQ ID NO 14
<211> LENGTH: 918
<212> TYPE: DNA
<213> ORGANISM: Glycine max

<400> SEQUENCE: 14
aagcttctgc agggtcgacg gcccgggctg gtcctccatt tgccgctcat taattaattt    60
gataacagcc gtaccgatca attacttatg cttcttccat cgtaattata tgcatgtcgg   120
ttcttttaat cttggtactc tcgaatgcca ccacaacact gactagtctc ttggatcatg   180
agaaaaagcc aaagaacaaa aagacaacaa taaagagtat cctttgcaaa aaatgtcta   240
agttcataaa atacaaacaa aaacgcaatc acacacagtg gacccaaaag ccatgcacaa   300
caacacgtac tcaccaaggt gcaatcgtgc tgcccaaaaa cattcaccaa ctcaatccat   360
gatgagccca cacatttgtt gtttgtaacc aaatctcaaa cgcggtgttc tctttggaaa   420
gcaaccatat cagcatatca cactatctag tctcttggat catgcatgcg caaccaaaag   480
acaacacata aagtatcctt tcgaaagcaa tgtccaagtc catcaaataa aattgagaca   540
aaatgcaacc tcaccccact tcactatcca tggctgatca agatcgccgc gtccatgtag   600
gtctaaatgc catgcacatc aacacgtact caacatgcag cccaaattgc tcaccatcgc   660
```

-continued

```
tcaacacatt tcttgttaat ttctaagtac actgcctatg cgactctaac tcgatcacaa      720
ccatcttccg tcacatcaat tttgttcaat tcaacacccg tcaacttgca tgccacccca      780
tgcatgcaag ttaacaagag ctatatctct tctatgacta taaatacccg caatctcggt      840
ccaggttttc atcatcgaga actagttcaa tatcctagta taccttaata aataatttaa      900
gatactagat ctccatgg                                                    918
```

<210> SEQ ID NO 15
<211> LENGTH: 547
<212> TYPE: DNA
<213> ORGANISM: Glycine max

<400> SEQUENCE: 15

```
ttaagatata ctatgatgag agcgcggttc ccattactgt tgctgggagt tgttttccta       60
gcatcagttt ctgtctcatt tggcattgcg tattgggaaa agcagaaccc cagtcacaac      120
aagtgcctcc gaagttgcaa tagcgagaaa gactcctaca ggaaccaagc atgccacgct      180
cgttgcaacc tccttaaggt ggaggaagaa gaagaatgcg aagaaggtca aattccacga      240
ccacgaccac aacacccgga gagggaacgt cagcaacacg gtgagaagga ggaagacgaa      300
ggtgagcagc cacgtccatt cccattccca cgcccacgcc aacctcatca agaggaagag      360
cacgagcaga aggaggaaca cgaatggcat cgcaaggagg aaaaacacgg aggaaaggga      420
agtgaagagg aacaagatga acgtgaacac ccacgcccac accaacctca tcaaaaggaa      480
gaggaaaagc acgaatggca acacaagcag gaaaagcacc aaggaaagga aagtgaagaa      540
gaagaag                                                                547
```

<210> SEQ ID NO 16
<211> LENGTH: 499
<212> TYPE: DNA
<213> ORGANISM: Glycine max

<400> SEQUENCE: 16

```
atgatgagag cacggttccc attactgttg ctgggacttg ttttcctggc ttcagtttct       60
gtctcatttg gcattgctta ctgggaaaaa gagaacccca aacacaacaa gtgtctccag      120
agttgcaata gcgagagaga ctcgtacagg aaccaagcat gccacgctcg ttgcaacctc      180
cttaaggtgg agaagaaga atgtgaagaa ggtgaaattc cacgaccacg accacgacca      240
caacacccgg agagggaacc tcagcaaccc ggtgagaagg aggaagacga agatgagcaa      300
ccacgtccaa tcccattccc acgccacaa cctcgtcaag aagaagagca cgagcagaga      360
gaggaacagg aatggcctcg caaggaggaa aaacgcggag aaaagggaag tgaagaggaa      420 gatgaggat aggatgagga acaagatgaa cgtcaattcc cattcccacg cccacctcat      480
cagaaggaag agcgaaacg                                                   499
```

SEED SPECIFIC 7Sα PROMOTER FOR EXPRESSING GENES IN PLANTS

This application claims priority to U.S. provisional application Ser. No. 60/316,975 filed Sep. 5, 2001.

The present invention relates to the field of plant genetics. More specifically, the present invention relates to seed specific gene expression.

Seeds provide an important source of dietary protein for humans and livestock. However, the protein content of seeds is often incomplete. For example, many seed proteins are deficient in one or more essential amino acids. This deficiency may be overcome by genetically modifying the native or non-native proteins to have a more nutritionally complete composition of amino acids (or some other desirable feature) and to overexpress the modified proteins in the transgenic plants. Alternatively, one or more genes could be introduced into a crop plant to manipulate it's metabolic pathways and modify the free amino acid content. These approaches are useful in producing crops exhibiting important agronomic traits, and nutritional, and pharmaceutical properties.

Despite the availability of many molecular tools, the genetic modification of seeds is often constrained by an insufficient accumulation of the engineered protein. Many intracellular processes may impact the overall protein accumulation, including transcription, translation, protein assembly and folding, methylation, phosphorylation, transport, and proteolysis. Intervention in one or more of these processes can increase the amount of protein produced in genetically engineered seeds.

Introduction of a gene can cause deleterious effect on plant growth and development. Under such circumstances, the expression of the gene may need to be limited to the desired target tissue. For example, it might be necessary to express an amino acid deregulation gene in a seed-specific fashion to avoid an undesired phenotype that may affect yield or other agronomic traits.

The promoter portion of a gene plays a central role in controlling gene expression. Along the promoter region, the transcription machinery is assembled and transcription is initiated. Transcription initiation at the promoter may be regulated in several ways. For example, a promoter may be induced by the presence of a particular compound, express a gene only in a specific tissue, or constitutively throughout the plant. Thus, transcription of a coding sequence may be modified by operably linking the coding sequence to promoters with different regulatory characteristics.

SUMMARY OF THE INVENTION

The present invention includes promoters capable of generating seed specific transcription, and methods of modifying, producing, and using the same. The invention also provides compositions, transformed host cells, transgenic plants, and seeds containing the high-expression promoters, and methods for preparing and using the same.

The present invention includes and provides a transformed plant containing a nucleic acid molecule that comprises in the 5' to 3' direction: a promoter having a nucleic acid sequence selected from the group consisting of SEQ ID NOs: 11, 12, 13 and 14 and complements thereof, and nucleic acid sequences that hybridize under stringent conditions to any of SEQ ID NOs: 11, 12, 13 and 14, and complements thereof. The present invention includes and provides a transformed plant containing a nucleic acid molecule that comprises in the 5' to 3' direction: a promoter having a nucleic acid sequence that exhibits an identity to a nucleic acid sequence selected from the group consisting of SEQ ID NOs: 11, 12, 13 and 14, and complements thereof of greater than about 90%, operably linked to a structural nucleic acid sequence, wherein the promoter is heterologous with respect to the structural nucleic acid sequence.

The present invention includes and provides a method of transforming a soybean plant comprising: providing a nucleic acid molecule that comprises in the 5' to 3' direction: a promoter having a nucleic acid sequence selected from the group consisting of SEQ ID NOs: 11, 12, 13 and 14, and complements thereof, and nucleic acid sequences that hybridize under stringent conditions to any of SEQ ID NOs: 11, 12, 13 and 14, and complements thereof, operably linked to a structural nucleic sequence; and transforming the plant with the nucleic molecule.

The present invention includes and provides a method of transforming a soybean plant comprising: providing a nucleic acid molecule that comprises in the 5' to 3' direction: a promoter having a nucleic acid sequence selected from the group consisting of SEQ ID NOs: 11, 12, 13 and 14, and complements thereof, and nucleic acid sequences that hybridize under stringent conditions to any of SEQ ID NOs: 11, 12, 13 and 14, and complements thereof of greater than about 90%, operably linked to a structural nucleic acid sequence, wherein the promoter is heterologous with respect to the structural nucleic acid sequence.

The present invention provides a method of expressing a structural nucleic acid molecule in a seed comprising: growing a transformed plant containing a nucleic acid molecule that comprises in the 5' to 3' direction: a promoter having a nucleic acid sequence selected from the group consisting of SEQ ID NOs: 11, 12, 13 and 14, and complements thereof, and nucleic acid sequences that hybridize under stringent conditions to any of SEQ ID NOs: 11, 12, 13 and 14, and complements thereof, operably linked to the structural nucleic acid molecule, wherein the transformed plant produces the seed and the structural nucleic acid molecule is transcribed in the seed; and isolating the seed.

The present invention provides a method of obtaining a seed enhanced in a product of a structural gene comprising: growing a transformed plant containing a nucleic acid molecule that comprises in the 5' to 3' direction: a promoter having a nucleic acid sequence selected from the group consisting of SEQ ID NOs: 11, 12, 13 and 14, and complements thereof, and nucleic acid sequences that hybridize under stringent conditions to any of SEQ ID NOs: 11, 12, 13 and 14, and complements thereof, operably linked to the structural nucleic acid molecule, wherein the transformed plant produces the seed and the structural nucleic acid molecule is transcribed in the seed; and isolating the seed from the transformed plant.

The present invention provides a method of obtaining meal enhanced in a product of a structural gene comprising: growing a transformed plant containing a nucleic acid molecule that comprises in the 5' to 3' direction: a promoter having a nucleic acid sequence selected from the group consisting of SEQ ID NOs: 11, 12, 13 and 14, and complements thereof, and nucleic acid sequences that hybridize under stringent conditions to any of SEQ ID NOs: 11, 12, 13 and 14, and complements thereof, operably linked to the structural nucleic acid molecule, wherein the transformed plant produces the seed and the structural nucleic acid molecule is transcribed in the seed; and preparing the meal comprising said transformed plant or part thereof.

The present invention provides a method of obtaining feedstock enhanced in a product of a structural gene comprising: growing a transformed plant containing a nucleic acid molecule that comprises in the 5' to 3' direction: a promoter having a nucleic acid sequence that hybridizes under stringent conditions with a nucleic acid sequence selected from the group consisting of SEQ ID NOs: 11, 12, 13 and 14, and complements thereof operably linked to the structural nucleic acid molecule, wherein the transformed plant produces the seed and the structural nucleic acid molecule is transcribed in the seed; and preparing the meal comprising the transformed plant or part thereof.

The present invention provides a method of obtaining oil enhanced in a product of a structural gene comprising: growing a transformed plant containing a nucleic acid molecule that comprises in the 5' to 3' direction: a promoter having a nucleic acid sequence that hybridizes under stringent conditions with a nucleic acid sequence selected from the group consisting of SEQ ID NOs: 11, 12, 13 and 14, and complements thereof operably linked to the structural nucleic acid molecule, wherein the transformed plant produces the seed and the structural nucleic acid molecule is transcribed in the seed; and isolating the oil.

The present invention includes and provides a substantially purified nucleic acid molecule comprising nucleic acid sequences selected from the group consisting of SEQ ID NOs: 11, 12, 13 and 14, and complements thereof.

The present invention includes and provides a vector comprising a nucleic acid sequence selected from the group consisting of SEQ ID NOs: 11, 12, 13 and 14, and complements thereof.

The present invention includes and provides a cell containing a vector comprising a nucleic acid sequence selected from the group consisting of SEQ ID NOs: 11, 12, 13 and 14, and complements thereof.

The present invention includes and provides a nucleic acid molecule capable of specifically hybridizing under stringent conditions to a nucleic acid molecule selected from the group consisting of SEQ ID NOs: 11, 12, 13 and 14, and complements thereof.

The present invention includes and provides a vector comprising a nucleic acid molecule capable of specifically hybridizing under stringent conditions to a nucleic acid molecule selected from the group consisting of SEQ ID NOs: 11, 12, 13 and 14, and complements thereof.

The present invention includes and provides a cell containing a vector comprising a nucleic acid molecule capable of specifically hybridizing under stringent conditions to a nucleic acid molecule selected from the group consisting of SEQ ID NOs: 11, 12, 13 and 14, and complements thereof.

The present invention includes and provides a substantially purified nucleic acid sequence that exhibits an identity to a nucleic acid sequence selected from the group consisting of SEQ ID NOs: 11, 12, 13 and 14, and complements thereof of greater than about 90%.

The present invention includes and provides a nucleic acid fragment comprising at least 20 consecutive nucleotides of a nucleic acid sequence selected from the group consisting of SEQ ID NOs: 11, 12, 13 and 14, and complements thereof.

The present invention includes and provides a nucleic acid fragment comprising at least 30 consecutive nucleotides of a nucleic acid sequence selected from the group consisting of SEQ ID NOs: 11, 12, 13 and 14, and complements thereof.

The present invention includes and provides a nucleic acid fragment comprising at least 50 consecutive nucleotides of a nucleic acid sequence selected from the group consisting of SEQ ID NOs: 11, 12, 13 and 14, and complements thereof.

The present invention includes and provides oil produced from one or more seeds of a transformed plant containing a nucleic acid molecule that comprises in the 5' to 3' direction: a promoter having a nucleic acid sequence selected from the group consisting of SEQ ID NOs: 11, 12, 13 and 14, and complements thereof, and nucleic acid sequences that hybridize under stringent conditions to any of SEQ ID NOs: 11, 12, 13 and 14, and complements thereof.

The present invention includes and provides oil produced from one or more seeds of a transformed plant containing a nucleic acid molecule that comprises in the 5' to 3' direction: a promoter having a nucleic acid sequence selected from the group consisting of SEQ ID NOs: 11, 12, 13 and 14, and complements thereof of greater than about 90%, and nucleic acid sequences that hybridize under stringent conditions to any of SEQ ID NOs: 11, 12, 13 and 14, and complements thereof, operably linked to a structural nucleic acid sequence, wherein the promoter is heterologous with respect to the structural nucleic acid sequence.

The present invention includes and provides a seed generated by a transformed plant containing a nucleic acid molecule that comprises in the 5' to 3' direction: a promoter having a nucleic acid sequence selected from the group consisting of SEQ ID NOs: 11, 12, 13 and 14, and complements thereof, and nucleic acid sequences that hybridize under stringent conditions to any of SEQ ID NOs: 11, 12, 13 and 14, and complements thereof.

The present invention includes and provides a seed generated by a transformed plant containing a nucleic acid molecule that comprises in the 5' to 3' direction: a promoter having a nucleic acid sequence selected from the group consisting of SEQ ID NOs: 11, 12, 13 and 14, and complements thereof of greater than about 90%, and nucleic acid sequences that hybridize under stringent conditions to any of SEQ ID NOs: 11, 12, 13 and 14, and complements thereof, operably linked to a structural nucleic acid sequence, wherein the promoter is heterologous with respect to the structural nucleic acid sequence.

The present invention includes and provides feedstock comprising a transformed plant or part thereof containing a nucleic acid molecule that comprises in the 5' to 3' direction: a promoter having a nucleic acid sequence selected from the group consisting of SEQ ID NOs: 11, 12, 13 and 14, and complements thereof, and nucleic acid sequences that hybridize under stringent conditions to any of SEQ ID NOs: 11, 12, 13 and 14, and complements thereof.

The present invention includes and provides feedstock comprising a transformed plant or part thereof containing a nucleic acid molecule that comprises in the 5' to 3' direction: a promoter having a nucleic acid sequence selected from the group consisting of SEQ ID NOs: 11, 12, 13 and 14, and complements thereof of greater than about 90%, and nucleic acid sequences that hybridize under stringent conditions to any of SEQ ID NOs: 11, 12, 13 and 14, and complements thereof, operably linked to a structural nucleic acid sequence, wherein the promoter is heterologous with respect to the structural nucleic acid sequence.

The present invention includes and provides a meal comprising plant material from a transformed plant containing a nucleic acid molecule that comprises in the 5' to 3' direction: a promoter having a nucleic acid sequence selected from the group consisting of SEQ ID NOs: 11, 12, 13 and 14, and complements thereof, and nucleic acid sequences that hybridize under stringent conditions to any of SEQ ID NOs: 11, 12, 13 and 14, and complements thereof.

The present invention includes and provides a meal comprising plant material from a transformed plant containing a nucleic acid molecule that comprises in the 5' to 3' direction: a promoter having a nucleic acid sequence selected from the group consisting of SEQ ID NOs: 11, 12, 13 and 14, and complements thereof of greater than about 90%, and nucleic acid sequences that hybridize under stringent conditions to any of SEQ ID NOs: 11, 12, 13 and 14, and complements thereof, operably linked to a structural nucleic acid sequence, wherein the promoter is heterologous with respect to the structural nucleic acid sequence.

The present invention includes and provides a container of seeds, wherein at least about 25% of said seeds comprises in the 5' to 3' direction: a promoter having a nucleic acid sequence selected from the group consisting of SEQ ID NOs: 11, 12, 13 and 14, and complements thereof of greater than about 90%, and nucleic acid sequences that hybridize under stringent conditions to any of SEQ ID NOs: 11, 12, 13 and 14, and complements thereof, operably linked to a structural nucleic acid sequence, wherein the promoter is heterologous with respect to the structural nucleic acid sequence.

BRIEF DESCRIPTION OF THE FIGURES

FIG. 1 sets forth a sequence alignment of two 7S alpha cDNA sequences.

FIG. 2a sets forth the sequence of p-GEM-T 1T.

FIG. 2b is a plasmid map for vector pMON55548.

FIG. 3a is a plasmid map for vector pMON8677.

FIG. 3b is a plasmid map for vector pMON55546.

FIG. 4 is a plasmid map for pMON55547.

FIG. 5 is a plasmid map for vector pMON55554.

FIG. 6 is a plasmid map for vector pMON55542.

FIG. 7 is a comparison between 7Sα promoter and tARC5 promoter.

FIG. 8 is a plasmid map for vector pMON55553.

FIG. 9 is a plasmid map for vector pMON55541.

BRIEF DESCRIPTION OF THE SEQUENCES

SEQ ID NO: 1 is a 7Sα promoter sequence from soybean (*Glycine max* L.).

SEQ ID NO: 2 is a 7Sα promoter sequence from soybean (*Glycine max* L.).

SEQ ID NO: 3 is a 7Sα promoter sequence from soybean (*Glycine max* L.).

SEQ ID NO: 4 is a 7Sα promoter sequence from soybean (*Glycine max* L.).

SEQ ID NO: 5 is an adapter primer (HindIII-PstI) for amplifying the soybean GlcA gene.

SEQ ID NO: 6 is a 7Sα primary primer for amplifying the soybean GlcA gene.

SEQ ID NO: 7 is a 7Sα nested (BglII/NcoI) primer for amplifying the soybean GlcA gene.

SEQ ID NO: 8 is a 7Sα primer (NcoI/BglII) designed for amplifying the primer region of the soybean GlcA gene.

SEQ ID NO: 9 is a 7Sα gene adapter primer.

SEQ ID NO: 10 is a 7Sα gene specific primer.

SEQ ID NO: 11 is a 7Sα promoter sequence from soybean (*Glycine max* L.).

SEQ ID NO: 12 is a 7Sα promoter sequence from soybean (*Glycine max* L.).

SEQ ID NO: 13 is a 7Sα promoter sequence from soybean (*Glycine max* L.).

SEQ ID NO: 14 is a 7Sα promoter sequence from soybean (*Glycine max* L.).

SEQ ID NO: 15 is a coding region from a 7Sα' subunit of β-conglycinin.

SEQ ID NO: 16 is a coding region from a 7Sα subunit of β-conglycinin.

DEFINITIONS

The following definitions are provided as an aid to understanding the detailed description of the present invention.

The phrases "coding sequence," "structural sequence," and "structural nucleic acid sequence" refer to a physical structure comprising an orderly arrangement of nucleic acids. The nucleic acids are arranged in a series of nucleic acid triplets that each form a codon. Each codon encodes for a specific amino acid. Thus, the coding sequence, structural sequence, and structural nucleic acid sequence encode a series of amino acids forming a protein, polypeptide, or peptide sequence. The coding sequence, structural sequence, and structural nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

The phrases "DNA sequence," "nucleic acid sequence," and "nucleic acid molecule" refer to a physical structure comprising an orderly arrangement of nucleic acids. The DNA sequence or nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

The term "expression" refers to the transcription of a gene to produce the corresponding mRNA and translation of this mRNA to produce the corresponding gene product (i.e., a peptide, polypeptide, or protein).

The term "expression of antisense RNA" refers to the transcription of a DNA to produce a first RNA molecule capable of hybridizing to a second RNA molecule. Formation of the RNA—RNA hybrid inhibits translation of the second RNA molecule to produce a gene product.

"Homology" refers to the level of similarity between two or more nucleic acid or amino acid sequences in terms of percent of positional identity (i.e., sequence similarity or identity). Homology also refers to the concept of similar functional properties among different nucleic acids or proteins.

The phrase "heterologous" refers to the relationship between two or more nucleic acid or protein sequences that are derived from different sources. For example, a promoter is heterologous with respect to a coding sequence if such a combination is not normally found in nature. In addition, a particular sequence may be "heterologous" with respect to a cell or organism into which it is inserted (i.e., does not naturally occur in that particular cell or organism).

"Hybridization" refers to the ability of a strand of nucleic acid to join with a complementary strand via base pairing. Hybridization occurs when complementary nucleic acid sequences in the two nucleic acid strands contact one another under appropriate conditions.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence.

The term "promoter" or "promoter region" refers to a nucleic acid sequence, usually found upstream (5') to a coding sequence, that is capable of directing transcription of a nucleic acid sequence into mRNA. The promoter or promoter region typically provide a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

The term "recombinant vector" refers to any agent such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source; is capable of genomic integration or autonomous replication.

"Regulatory sequence" refers to a nucleotide sequence located upstream (5'), within, or downstream (3') to a coding sequence. Transcription and expression of the coding sequence is typically impacted by the presence or absence of the regulatory sequence.

The term "substantially homologous" refers to two sequences which are at least about 90% identical in sequence, as measured by the BestFit program described herein (Version 10; Genetics Computer Group, Inc., University of Wisconsin Biotechnology Center, Madison, Wis.), using default parameters.

The term "transformation" refers to the introduction of nucleic acid into a recipient host. The term "host" refers to bacteria cells, fungi, animals or animal cells, plants or seeds, or any plant parts or tissues including plant cells, protoplasts, calli, roots, tubers, seeds, stems, leaves, seedlings, embryos, and pollen.

As used herein, the term "transgenic plant" refers to a plant where an introduced nucleic acid is stably introduced into a genome of the plant, for example, the nuclear or plastid genomes.

As used herein, the term "substantially purified" refers to a molecule separated from substantially all other molecules normally associated with it in its native state. More preferably a substantially purified molecule is the predominant species present in a preparation. A substantially purified molecule may be greater than about 60% free, preferably about 75% free, more preferably about 90% free, and most preferably about 95% free from the other molecules (exclusive of solvent) present in the natural mixture. The term "substantially purified" is not intended to encompass molecules present in their native state.

DETAILED DESCRIPTION OF THE PREFERRED EMBODIMENTS

The present invention provides promoters capable of transcribing a heterologous structural nucleic acid sequence in a seed, and methods of modifying, producing, and using the same. The invention also provides compositions, transformed host cells and plants containing seed specific promoters, and methods for preparing and using the same.

Nucleic Acid Molecules

The present invention provides nucleic acid molecules that hybridize to a nucleic acid molecule having a nucleic acid sequence selected from the group SEQ ID NOs: 11, 12, 13 and 14, and complements thereof. The present invention also includes nucleic acid molecules that are fragments of such molecules.

Nucleic acid hybridization is a technique well known to those of skill in the art of DNA manipulation. The hybridization property of a given pair of nucleic acids is an indication of their similarity or identity.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C.

High stringency conditions may be used to select for nucleic acid sequences with higher degrees of identity to the disclosed nucleic acid sequences (Sambrook et al., 1989). (Note: Full citations for all references are provided herein below.)

The high stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50×stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. The high stringency conditions are preferably provided by 6×SSC, 5×Denhardt's solution, 100 mg/mL fish sperm DNA, and 0.1% (w/v) SDS, with an incubation at 55° C. for several hours.

The hybridization is generally followed by several wash steps. The wash compositions generally comprise 0.5× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C.

The nucleic acid molecules preferably hybridize, under low or high stringency conditions, with a nucleic acid sequence selected from the group consisting of SEQ ID NOs: 11, 12, 13 and 14, and complements thereof. The nucleic acid molecules most preferably hybridize under high stringency conditions with a nucleic acid sequence selected from the group consisting of SEQ ID NOs: 11, 12, 13 and 14, and complements thereof. Exemplary nucleic acid molecules include promoters having nucleic acid sequences of SEQ ID NOs: 11, 12, 13 and 14, the complements thereof, or any fragments thereof.

In an alternative embodiment, the nucleic acid molecule comprises a nucleic acid sequence that is greater than about 85% identical, and more preferably greater than about 86, about 87, about 88, about 89, about 90, about 91, about 92, about 93, about 94, about 95, about 96, about 97, about 98, or about 99% identical to a nucleic acid sequence selected from the group consisting of SEQ ID NOs: 11, 12, 13 and 14, and complements thereof and fragments of either.

The percent of sequence identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, 1981; Smith et al., 1983). The percent identity is most preferably determined using the "Best Fit" program using default parameters.

The present invention also provides nucleic acid molecule fragments that hybridize under low or high stringency conditions to nucleic acid molecules having a nucleic acid sequence selected from the group consisting of SEQ ID NOs: 11, 12, 13 and 14, and complements thereof, fragments of nucleic acid molecules and that exhibit greater than about 80, about 85, about 90, about 95 or about 99% sequence identity with a nucleic acid sequence selected from the group consisting of SEQ ID NOs: 11, 12, 13 and 14, and complements thereof, or fragments of any of these molecules.

In an embodiment, the fragments are between about 3000 and about 1000 consecutive nucleotides, about 1800 and about 150 consecutive nucleotides, about 1500 and about 500 consecutive nucleotides, about 1300 and about 250 consecutive nucleotides, about 1000 and about 200 consecutive nucleotides, about 800 and about 150 consecutive nucleotides, about 500 and about 100 consecutive nucleotides, about 300 and about 75 consecutive nucleotides, about 100 and about 50 consecutive nucleotides, about 50 and about 25 consecutive nucleotides, or about 20 and about 10 consecutive nucleotides long of a nucleic molecule of the present invention.

In another embodiment, the fragment comprises at least about 20, about 30, about 40, about 50, about 60, about 70, about 80, about 90, about 100, about 150, about 200, about 250 about 500, or about 750 consecutive nucleotides of a nucleic acid sequence of the present invention.

Promoters

In a preferred embodiment any of the disclosed nucleic acid molecules may be promoters. In a particularly preferred embodiment, the promoter is a 7Sα promoter. In an embodiment, the promoter is tissue or organ specific, preferably seed specific. In a particularly preferred embodiment the promoter preferentially expresses associated structural genes in the endosperm or embryo.

In one aspect, a promoter is considered tissue or organ specific if the level of an mRNA in that tissue or organ is expressed at a level that is at least 10 fold higher, preferably at least about 100 fold higher or at least about 1,000 fold higher than another tissue or organ. The level of mRNA can be measured either at a single time point or at multiple time points and as such the fold increase can be average fold increase or an extrapolated value derived from experimentally measured values. As it is a comparison of levels, any method that measures mRNA levels can be used. In a preferred aspect, the tissue or organs compared are a seed or seed tissue with a leaf or leaf tissue. In another preferred aspect, multiple tissues or organs are compared. A preferred multiple comparison is a seed or seed tissue compared with two, three, four or more tissues or organs selected from the group consisting of floral tissue, floral apex, pollen, leaf, embryo, shoot, leaf primodia, shoot apex, root, root tip, vascular tissue and cotyledon. As used herein, examples of plant organs are seed, leaf, root, etc. and example of tissues are leaf primodia, shoot apex, vascular tissue etc.

The activity or strength of a promoter may be measured in terms of the amount of mRNA or protein accumulation it specifically produces, relative to the total amount of mRNA or protein. The promoter preferably expresses an operably linked nucleic acid sequence at a level greater than about 2.5%; more preferably greater than about 5, about 6, about 7, about 8, or about 9%; even more preferably greater than about 10, about 11, about 12, about 13, about 14, about 15, about 16, about 17, about 18, or about 19%; and most preferably greater than about 20% of the total mRNA.

Alternatively, the activity or strength of a promoter may be expressed relative to a well-characterized promoter (for which transcriptional activity was previously assessed). For example, a promoter of interest may be operably linked to a reporter sequence (e.g., GUS) and introduced into a specific cell type. A known promoter may be similarly prepared and introduced into the same cellular context. Transcriptional activity of the promoter of interest is then determined by comparing the amount of reporter expression, relative to the known promoter. The cellular context is preferably soybean.

Structural Nucleic Acid Sequences

The promoters of the present invention may be operably linked to a second nucleic acid sequence that is heterologous with respect to the nucleic acid sequence of the promoter. The second nucleic acid sequence may generally be any nucleic acid sequence for which an increased level of transcription is desired. The second nucleic acid sequence preferably encodes a polypeptide that is suitable for incorporation into the diet of a human or an animal or provides some other agriculturally important feature.

Suitable second nucleic acid sequences include, without limitation, those encoding seed storage proteins, fatty acid pathway enzymes, tocopherol biosynthetic enzymes, amino acid biosynthetic enzymes, and starch branching enzymes.

Preferred seed storage proteins include zeins (U.S. Pat. Nos. 4,886,878, 4,885,357, 5,215,912, 5,589,616, 5,508, 468, 5,939,599, 5,633,436 and 5,990,384;: WO 90/01869, WO 91/13993, WO 92/14822, WO 93/08682, WO 94/20628, WO 97/28247, WO 98/26064 and WO 99/40209), 7S proteins (U.S. Pat. Nos. 5,003,045 and 5,576,203) brazil nut protein (U.S. Pat. No. 5,850,024), phenylalanine free proteins (WO 96/17064), albumin (WO 97/35023), β-conglycinin (WO 00/19839), 11S (U.S. Pat. No. 6,107, 051), alpha-hordothionin (U.S. Pat. Nos. 5,885,802 and 5,885,801) arcelin seed storage proteins (U.S. Pat. No. 5,270,200) lectins (U.S. Pat. No. 6,110,891) and glutenin (U.S. Pat. Nos. 5,990,389 and 5,914,450).

Preferred fatty acid pathway enzymes include thioesterases (U.S. Pat. Nos. 5,512,482, 5,530,186, 5,945, 585, 5,639,790, 5,807,893, 5,955,650, 5,955,329, 5,759,829, 5,147,792, 5,304,481, 5,298,421, 5,344,771 and 5,760,206), and desaturases (U.S. Pat. Nos. 5,689,050, 5,663,068, 5,614, 393, 5,856,157, 6,117,677, 6,043,411, 6,194,167, 5,705,391, 5,663,068, 5,552,306, 6,075,183, 6,051,754, 5,689,050, 5,789,220, 5,057,419, 5,654,402, 5,659,645, 6,100,091, 5,760,206, 6,172,106, 5,952,544, 5,866,789, 5,443,974 and 5,093,249). Preferred tocopherol biosynthetic enzymes include tyrA, slr173, ATPT2, dxs, dxr, GGPPS, HPPD, GMT, MT1, AANT1, slr 1737, and an antisense construct for homogentisic acid dioxygenase (Kridl et al.,*Seed Sci. Res.* 1:209:219 (1991); Keegstra, *Cell* 56(2):247–53 (1989); Nawrath, et al., *Proc. Natl. Acad. Sci. U.S.A.* 91:12760–12764 (1994); Xia et al., *J. Gen. Microbiol.* 138:1309–1316 (1992); Lois et al., *Proc. Natl. Acad. Sci. U.S.A.* 95(5):2105–2110 (1998); Takahashi et al. *Proc. Natl. Acad. Sci. U.S.A.* 95(17), 9879–9884 (1998); Norris et al., *Plant Physiol.* 117:1317–1323 (1998); Bartley and Scolnik, *Plant Physiol.* 104:1469–1470 (1994), Smith et al., *Plant J.* 11:83–92 (1997); WO 00/32757; WO 00/10380; Saint Guily, et al., *Plant Physiol.*, 100(2):1069–1071 (1992); Sato et al., *J. DNA Res.* 7(1):31–63 (2000)).

Preferred amino acid biosynthetic enzymes include anthranilate synthase (U.S. Pat. No. 5,965,727 and WO 97/26366, WO 99/11800, and WO 99/49058) tryptophan decarboxylase (WO 99/06581) and threonine decarboxylase (U.S. Pat. Nos. 5,534,421 and 5,942,660 and WO 95/19442), threonine deaminase (WO 99/02656 and WO 98/55601), dihydrodipicolinate synthase (U.S. Pat. No. 5,367,110), lysine ketoglutarate reductase (WO 98/42831) and aspartate kinase (U.S. Pat. Nos. 5,367,110, 5,858,749 and 6,040,160).

Preferred starch branching enzymes include those set forth in U.S. Pat. Nos. 6,232,122 and 6,147,279, and WO 97/22703.

Alternatively, a promoter and second nucleic acid sequence may be designed to down-regulate a specific nucleic acid sequence. This is typically accomplished by linking the promoter to a second nucleic acid sequence that is oriented in the antisense direction. One of ordinary skill in the art is familiar with such antisense technology. Any nucleic acid sequence may be negatively regulated in this manner.

One of ordinary skill in the art will also recognize that a promoter of the instant invention may also be designed to down-regulate a specific nucleic acid sequence using the phenomenon of cosuppression. Cosuppression of an endogenous gene using both full and partial length cDNA sequences has been described (Napoli et al. *The Plant Cell* 2:279–289 (1990)).

Additonally, expression of a specific nucleic acid sequence can also be down regulated by the non-coding regions of said nucleic acid sequence. One skilled in the art can readily isolate genomic DNA containing sequences that flank the coding region of said nucleic acid sequence, or introns of said coding region, and use the non-coding regions for antisense or cosuppression inhibition.

Targets of such regulation may include polypeptides that have a low content of essential amino acids, yet are expressed at a relatively high level in a particular tissue. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived feed or to down-regulate catabolic enzymes involved in degradation of desired compounds such as essential amino acids.

Modified Structural Nucleic Acid Sequences

The promoters of the present invention may also be operably linked to a modified structural nucleic acid sequence that is heterologous with respect to the promoter. The structural nucleic acid sequence may be modified to provide various desirable features. For example, a structural nucleic acid sequence may be modified to increase the content of essential amino acids, enhance translation of the amino acid sequence, alter post-translational modifications (e.g., phosphorylation sites), transport a translated product to a compartment inside or outside of the cell, improve protein stability, insert or delete cell signaling motifs, etc.

In a preferred embodiment, the structural nucleic acid sequence is enhanced to encode a polypeptide having an increased content of at least one, and more preferably about 2, about 3, or about 4 of the essential amino acids selected from the group consisting of histidine, lysine, methionine, and phenylalanine. Non-essential amino acids may also be added, as needed, for structural and nutritive enhancement of the polypeptide. Structural nucleic acid sequences particularly suited to such enhancements include those encoding native polypeptides that are expressed at relatively high levels, have a particularly low content of essential amino acids, or both. An example of such are the seed storage proteins, such as glycinin and β-conglycinin. Other suitable targets include arcelin, phaseolin, lectin, zeins, and albumin.

Codon Usage in Structural Nucleic Acid Sequences

Due to the degeneracy of the genetic code, different nucleotide codons may be used to code for a particular amino acid. A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any of the above described nucleic acid and amino acid sequences may be modified to reflect the preferred codon usage of a host cell or organism in which they are contained. Modification of a structural nucleic acid sequence for optimal codon usage in plants is described in U.S. Pat. No. 5,689,052.

Other Modifications of Structural Nucleic Acid Sequences

Additional variations in the structural nucleic acid sequences described above may encode proteins having equivalent or superior characteristics when compared to the proteins from which they are engineered. Mutations may include deletions, insertions, truncations, substitutions, fusions, shuffling of motif sequences, and the like.

Mutations to a structural nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a structural nucleic acid sequence. Examples include single strand rescue (Kunkel et al., 1985), unique site elimination (Deng and Nickloff, 1992), nick protection (Vandeyar et al., 1988), and PCR (Costa et al., 1996). Random or non-specific mutations may be generated by chemical agents (for a general review, see Singer and Kusmierek, 1982) such as nitrosoguanidine (Cerda-Olmedo et al., 1968; Guerola et al., 1971) and 2-aminopurine (Rogan and Bessman, 1970); or by biological methods such as passage through mutator strains (Greener et al., 1997). Additional methods of making the alterations described above are described by Ausubel et al. (1995); Bauer et al. (1985); Craik (1985); Frits Eckstein et al. (1982); Sambrook et al. (1989); Smith et al. (1981); and Osuna et al. (1994).

The modifications may result in either conservative or non-conservative changes in the amino acid sequence. Conservative changes are changes which do not alter the final amino acid sequence of the protein. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between about 1 and about 5 conservative changes.

Non-conservative changes include additions, deletions, and substitutions which result in an altered amino acid sequence. In a preferred embodiment, the protein has between about 5 and about 500 non-conservative amino acid changes, more preferably between about 10 and about 300 non-conservative amino acid changes, even more preferably between about 25 and about 150 non-conservative amino acid changes, and most preferably between about 5 and about 25 non-conservative amino acid changes or between about 1 and about 5 non-conservative changes.

Modifications may be made to the protein sequences described herein and the nucleic acid sequences which encode them that maintain the desired properties of the molecule. The following is a discussion based upon changing the amino acid sequence of a protein to create an equivalent, or possibly an improved, second-generation molecule. The amino acid changes may be achieved by changing the codons of the structural nucleic acid sequence, according to the codons given in Table 1.

TABLE 1

Codon degeneracy of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

Certain amino acids may be substituted for other amino acids in a protein sequence without appreciable loss of the desired activity. It is thus contemplated that various changes may be made in peptide sequences or protein sequences, or their corresponding nucleic acid sequences without appreciable loss of the biological activity.

In making such changes, the hydropathic index of amino acids may be considered. The importance of the hydropathic amino acid index in conferring interactive biological function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics. These are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted proteins have improved rumen resistance, increased resistance to proteolytic degradation, or both improved rumen resistance and increased resistance to proteolytic degradation, relative to the unmodified polypeptide from which they are engineered. Alternatively, changes could be made to improve kinetics of metabolic enzymes.

In a preferred aspect, the protein modified is selected from seed storage proteins, fatty acid pathway enzymes, tocopherol biosynthetic enzymes, amino acid biosynthetic enzymes and starch branching enzymes.

Recombinant Vectors

Any of the promoters and structural nucleic acid sequences described above may be provided in a recombinant vector. A recombinant vector typically comprises, in a 5' to 3' orientation: a promoter to direct the transcription of a structural nucleic acid sequence and a structural nucleic acid sequence. Suitable promoters and structural nucleic acid sequences include those described herein. The recombinant vector may further comprise a 3' transcriptional terminator, a 3' polyadenylation signal, other untranslated nucleic acid sequences, transit and targeting nucleic acid sequences, selectable markers, enhancers, and operators, as desired.

Means for preparing recombinant vectors are well known in the art. Methods for making recombinant vectors particularly suited to plant transformation are described in U.S. Pat. Nos. 4,971,908, 4,940,835, 4,769,061 and 4,757,011. These types of vectors have also been reviewed (Rodriguez et al., 1988; Glick et al., 1993).

Typical vectors useful for expression of nucleic acids in higher plants are well known in the art and include vectors derived from the tumor-inducing (Ti) plasmid of *Agrobacterium tumefaciens* (Rogers et al., 1987). Other recombinant vectors useful for plant transformation, including the pCaMVCN transfer control vector, have also been described (Fromm et al., 1985).

In one embodiment, multiple 7Sα promoters are operably linked in a single construct to any combination of structural genes. In a preferred embodiment, any combination of one, two, three, four, five, or six or more of SEQ ID NOs: 11, 12, 13 and 14 can be operatively linked in a single construct to any combination of structural genes.

Additional Promoters in the Recombinant Vector

One or more additional promoters may also be provided in the recombinant vector. These promoters may be operably linked, for example, without limitation, to any of the structural nucleic acid sequences described above. Alternatively, the promoters may be operably linked to other nucleic acid sequences, such as those encoding transit peptides, selectable marker proteins, or antisense sequences.

These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity. In plants, promoters that are inducible, of viral or synthetic origin, constitutively active, temporally regulated, and spatially regulated have been described (Poszkowski et al., 1989; Odell et al., 1985; Chau et al., 1989).

Often-used constitutive promoters include the CaMV 35S promoter (Odell et al., 1985), the enhanced CaMV 35S promoter, the Figwort Mosaic Virus (FMV) promoter (Richins et al., 1987), the mannopine synthase (mas) promoter, the nopaline synthase (nos) promoter, and the octopine synthase (ocs) promoter.

Useful inducible promoters include promoters induced by salicylic acid or polyacrylic acids (PR-1; Williams et al, 1992), induced by application of safeners (substituted benzenesulfonamide herbicides; Hershey and Stoner, 1991), heat-shock promoters (Ou-Lee et al., 1986; Ainley et al., 1990), a nitrate-inducible promoter derived from the spinach nitrite reductase structural nucleic acid sequence (Back et al., 1991), hormone-inducible promoters (Yamaguchi-Shinozaki et al., 1990; Kares et al., 1990), and light-inducible promoters associated with the small subunit of RuBP carboxylase and LHCP families (Kuhlemeier et al., 1989; Feinbaum et al., 1991; Weisshaar et al., 1991; Lam and Chua, 1990; Castresana et al., 1988; Schulze-Lefert et al., 1989).

Examples of useful tissue or organ specific promoters include β-conglycinin, (Doyle et al., 1986; Slighton and Beachy, 1987), and other seed specific promoters (Knutzon et al., 1992; Bustos et al., 1991; Lam and Chua, 1991). Plant functional promoters useful for preferential expression in seed plastid include those from plant storage proteins and from proteins involved in fatty acid biosynthesis in oilseeds. Examples of such promoters include the 5' regulatory regions from such structural nucleic acid sequences as napin (Kridl et al., 1991), phaseolin, zein, soybean trypsin inhibitor, ACP, stearoyl-ACP desaturase, and oleosin. Seed-specific regulation is further discussed in EP 0 255 378.

Another exemplary seed specific promoter is a lectin promoter. The lectin protein in soybean seeds is encoded by a single structural nucleic acid sequence (Le1) that is only expressed during seed maturation. A lectin structural nucleic acid sequence and seed-specific promoter have been characterized and used to direct seed specific expression in transgenic tobacco plants (Vodkin et al., 1983; Lindstrom et al., 1990).

Particularly preferred additional promoters in the recombinant vector include the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco (Mandel et al., 1995); corn sucrose synthetase 1 (Yang and Russell, 1990); corn alcohol dehydrogenase 1 (Vogel et al., 1989); corn light harvesting complex (Simpson, 1986); corn heat shock protein (Odell et al., 1985); the chitinase promoter from Arabidopsis (Samac et al., 1991); the LTP (Lipid Transfer Protein) promoters from broccoli (Pyee et al., 1995); petunia chalcone isomerase (Van Tunen et al., 1988); bean glycine rich protein 1 (Keller et al., 1989); potato patatin (Wenzler et al., 1989); the ubiquitin promoter from maize (Christensen et al., 1992); and the actin promoter from rice (McElroy et al., 1990).

An additional promoter is preferably seed selective, tissue selective, constitutive, or inducible. The promoter is most preferably the nopaline synthase (nos), octopine synthase (ocs), mannopine synthase (mas), cauliflower mosaic virus 19S and 35S (CaMV19S, CaMV35S), enhanced CaMV (eCaMV), ribulose 1,5-bisphosphate carboxylase (ssRUBISCO), figwort mosaic virus (FMV), CaMV derived AS4, tobacco RB7, wheat POX1, tobacco EIF-4, lectin protein (Le1), or rice RC2 promoter.

Recombinant Vectors having Additional Structural Nucleic Acid Sequences

The recombinant vector may also contain one or more additional structural nucleic acid sequences. These additional structural nucleic acid sequences may generally be any sequences suitable for use in a recombinant vector. Such structural nucleic acid sequences include, without limitation, any of the structural nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e., a single operon).

The additional structural nucleic acid sequences include, without limitation, those encoding seed storage proteins, fatty acid pathway enzymes, tocopherol biosynthetic enzymes, amino acid biosynthetic enzymes, and starch branching enzymes.

Preferred seed storage proteins include zeins (U.S. Pat. Nos. 4,886,878, 4,885,357, 5,215,912, 5,589,616, 5,508, 468, 5,939,599, 5,633,436 and 5,990,384; WO 90/01869, WO 91/13993, WO 92/14822, WO 93/08682, WO 94/20628, WO 97/28247, WO 98/26064 and WO 99/40209), 7S proteins (U.S. Pat. Nos. 5,003,045 and 5,576,203) brazil nut protein (U.S. Pat. No. 5,850,024), phenylalanine free proteins (WO 96/17064), albumin (WO 97/35023), β-conglycinin (WO 00/19839), 11S (U.S. Pat. No. 6,107, 051), alpha-hordothionin (U.S. Pat. Nos. 5,885,802 and 5,885,801) arcelin seed storage proteins (U.S. Pat. No. 5,270,200) lectins (U.S. Pat. No. 6,110,891) and glutenin (U.S. Pat. Nos. 5,990,389 and 5,914,450).

Preferred fatty acid pathway enzymes include thioesterases (U.S. Pat. Nos. 5,512,482, 5,530,186, 5,945, 585, 5,639,790, 5,807,893, 5,955,650, 5,955,329, 5,759,829, 5,147,792, 5,304,481, 5,298,421, 5,344,771 and 5,760,206), and desaturases (U.S. Pat. Nos. 5,689,050, 5,663,068, 5,614, 393, 5,856,157, 6,117,677, 6,043,411, 6,194,167, 5,705,391, 5,663,068, 5,552,306, 6,075,183, 6,051,754, 5,689,050, 5,789,220, 5,057,419, 5,654,402, 5,659,645, 6,100,091, 5,760,206, 6,172,106, 5,952,544, 5,866,789, 5,443,974 and 5,093,249).

Preferred tocopherol biosynthetic enzymes include tyrA, slr1 736, A TPT2, dxs, dxr, GGPPS, HPPD, GMT, MT1, AANT1, slr 1737, and an antisense construct for homogentisic acid dioxygenase (Kridl et al., *Seed Sci. Res.* 1:209:219 (1991); Keegstra, *Cell* 56(2):247–53 (1989); Nawrath, et al., *Proc. Natl. Acad. Sci. U.S.A.* 91:12760–12764 (1994); Xia et al., *J. Gen. Microbiol.* 138:1309–1316 (1992); Cyanobase http://www.kazusa.or.jp/cyanobase; Lois et al., *Proc. Natl. Acad. Sci. U.S.A.* 95(5):2105–21 10 (1998); Takahashi et al., *Proc. Natl. Acad. Sci. U.S.A.* 95(17), 9879–9884 (1998); Norris et al., *Plant Physiol.* 117:1317–1323 (1998); Bartley and Scolnik, *Plant Physiol.* 104:1469–1470 (1994), Smith et al., *Plant J.* 11:83–92 (1997); WO 00/32757; WO 00/10380; Saint Guily, et al., *Plant Physiol.*, 100(2):1069–1071 (1992); Sato et al., *J. DNA Res.* 7(1):31–63 (2000)).

Preferred amino acid biosynthetic enzymes include anthranilate synthase (U.S. Pat. No. 5,965,727, and WO 97/26366, WO 99/11800 and WO 99/49058) tryptophan decarboxylase (WO 99/06581) and threonine decarboxylase (U.S. Pat. Nos. 5,534,421 and 5,942,660, and WO 95/19442), threonine deaminase (WO 99/02656 and WO 98/55601) and aspartate kinase (U.S. Pat. Nos. 5,367,110, 5,858,749 and 6,040,160).

Preferred starch branching enzymes include those set forth in U.S. Pat. Nos. 6,232,122 and 6,147, 279, and WO 97/22703.

Alternatively, the second structural nucleic acid sequence may be designed to down-regulate a specific nucleic acid sequence. This is typically accomplished by operably linking the second structural amino acid, in an antisense orientation, with a promoter. One of ordinary skill in the art is familiar with such antisense technology. Any nucleic acid sequence may be negatively regulated in this manner. Preferable target nucleic acid sequences contain a low content of essential amino acids, yet are expressed at relatively high levels in particular tissues. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived foodstuffs, or to down-regulate catabolic enzymes involved in degradation of desired compounds such as essential amino acids.

Selectable Markers

A vector or construct may also include a selectable marker. Selectable markers may also be used to select for plants or plant cells that contain the exogenous genetic material. Examples of such include, but are not limited to: a neo gene (Potrykus et al., 1985), which codes for kanamycin resistance and can be selected for using kanamycin, RptII, G418, hpt etc.; a bar gene which codes for bialaphos resistance; a mutant EPSP synthase gene (Hinchee et al., 1988; Reynaerts et al., 1988), aadA (Jones et al., 1987) which encodes glyphosate resistance; a nitrilase gene which confers resistance to bromoxynil (Stalker et al., 1988); a mutant acetolactate synthase gene (ALS) which confers imidazolinone or sulphonylurea resistance (European Patent Application 154,204, 1985), ALS (D'Halluin et al., 1992), and a methotrexate resistant DHFR gene (Thillet et al., 1988). The selectable marker is preferably GUS, green fluorescent protein (GFP), neomycin phosphotransferase II (nptII), luciferase (LUX), an antibiotic resistance coding sequence, or an herbicide (e.g., glyphosate) resistance coding sequence. The selectable marker is most preferably a kanamycin, hygromycin, or herbicide resistance marker.

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, 1987); an R-locus gene, which encodes a product that regulates the production of anthocyanin pigments (red color) in plant tissues (Dellaporta et al., 1988); a β-lactamase gene (Sutcliffe et al., 1978), a gene which encodes an enzyme for which various chromogenic substrates are known (e.g., PADAC, a chromogenic cephalosporin); a luciferase gene (Ow et al., 1986); a xylE gene (Zukowsky et al., 1983) which encodes a catechol dioxygenase that can convert chromogenic catechols; an α-amylase gene (Ikatu et al., 1990); a tyrosinase gene (Katz et al., 1983) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

Other Elements in the Recombinant Vector

Various cis-acting untranslated 5' and 3' regulatory sequences may be included in the recombinant nucleic acid vector. Any such regulatory sequences may be provided in a recombinant vector with other regulatory sequences. Such combinations can be designed or modified to produce desirable regulatory features.

A 3' non-translated region typically provides a transcriptional termination signal, and a polyadenylation signal which functions in plants to cause the addition of adenylate nucleotides to the 3' end of the mRNA. These may be obtained from the 3' regions of the nopaline synthase (nos) coding sequence, a soybean 7Sα' storage protein coding sequence, the arcelin-5 coding sequence, the albumin coding sequence, and the pea ssRUBISCO E9 coding sequence. Typically, nucleic acid sequences located a few hundred base pairs downstream of the polyadenylation site serve to terminate transcription. These regions are required for efficient polyadenylation of transcribed mRNA.

Translational enhancers may also be incorporated as part of the recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Preferred 5' nucleic acid sequences include dSSU 5', PetHSP70 5', and GmHSP17.9 5' (U.S. Pat. No. 5,362,865).

The recombinant vector may further comprise a nucleic acid sequence encoding a transit peptide. This peptide may be useful for directing a protein to the extracellular space, a plastid, or to some other compartment inside or outside of the cell. (see, e.g., EP 0 218 571, U.S. Pat. Nos. 4,940,835, 5,88,624, 5,610,041, 5,618,988 and 6,107,060).

The structural nucleic acid sequence in the recombinant vector may comprise introns. The introns may be heterologous with respect to the structural nucleic acid sequence. Preferred introns include the rice actin intron and the corn HSP70 intron.

Fusion Proteins

Any of the above described structural nucleic acid sequences, and modified forms thereof, may be linked with additional nucleic acid sequences to encode fusion proteins. The additional nucleic acid sequence preferably encodes at least 1 amino acid, peptide, or protein. Many possible fusion combinations exist.

For instance, the fusion protein may provide a "tagged" epitope to facilitate detection of the fusion protein, such as GST, GFP, FLAG, or polyHIS. Such fusions preferably encode between about 1 and about 50 amino acids, more preferably between about 5 and about 30 additional amino acids, and even more preferably between about 5 and about 20 amino acids.

Alternatively, the fusion may provide regulatory, enzymatic, cell signaling, or intercellular transport functions. For example, a sequence encoding a plastid transit peptide may be added to direct a fusion protein to the chloroplasts within seeds. Such fusion partners preferably encode between about 1 and about 1000 additional amino acids, more preferably between about 5 and about 500 additional amino acids, and even more preferably between about 10 and about 250 amino acids.

Sequence Analysis

In the present invention, sequence similarity or identity is preferably determined using the "Best Fit" or "Gap" programs of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences. Optimal alignments are found by inserting gaps to maximize the number of matches using the local homology algorithm of Smith and Waterman (Smith and Waterman, 1981; Smith et al., 1983).

The Sequence Analysis Software Package described above contains a number of other useful sequence analysis tools for identifying homologues of the presently disclosed nucleotide and amino acid sequences. For example, the "BLAST" program searches for sequences similar to a query sequence (either peptide or nucleic acid) in a specified database (e.g., sequence databases maintained at the National Center for Biotechnology Information (NCBI) in Bethesda, Md., USA); "FastA" (Lipman and Pearson, 1985; see also Pearson and Lipman, 1988; Pearson, 1990) performs a Pearson and Lipman search for similarity between a query sequence and a group of sequences of the same type (nucleic acid or protein); "TfastA" performs a Pearson and Lipman search for similarity between a protein query sequence and any group of nucleotide sequences (it translates the nucleotide sequences in all six reading frames before performing the comparison); "FastX" performs a Pearson and Lipman search for similarity between a nucleotide query sequence and a group of protein sequences, taking frameshifts into account. "TfastX" performs a Pearson and Lipman search for similarity between a protein query sequence and any group of nucleotide sequences, taking frameshifts into account (it translates both strands of the nucleic acid sequence before performing the comparison).

Probes and Primers

Short nucleic acid sequences having the ability to specifically hybridize to complementary nucleic acid sequences may be produced and utilized in the present invention. Such short nucleic acid molecules may be used as probes to identify the presence of a complementary nucleic acid sequence in a given sample. Thus, by constructing a nucleic acid probe which is complementary to a small portion of a particular nucleic acid sequence, the presence of that nucleic acid sequence may be detected and assessed.

Alternatively, the short nucleic acid sequences may be used as oligonucleotide primers to amplify or mutate a complementary nucleic acid sequence using PCR technology. These primers may also facilitate the amplification of related complementary nucleic acid sequences (e.g., related nucleic acid sequences from other species).

Short nucleic acid sequences may be used as primers and specifically as PCR primers. A PCR probe is a nucleic acid molecule capable of initiating a polymerase activity while in a double-stranded structure with another nucleic acid. Various methods for determining the structure of PCR primers and PCR techniques exist in the art. Computer generated searches using programs such as Primer3, and STSPipeline (Whitehead Institute Center for Genome Research, Cambridge, Mass.) or GeneUp (Pesole et al., 1998), for example, can be used to identify potential PCR primers.

Any of the nucleic acid sequences disclosed herein may be used as a primer or probe. Use of these probes or primers may greatly facilitate the identification of transgenic plants which contain the presently disclosed promoters and structural nucleic acid sequences. Such probes or primers may also be used to screen cDNA or genomic libraries for additional nucleic acid sequences related to or sharing homology with the presently disclosed promoters and structural nucleic acid sequences.

A primer or probe is generally complementary to a portion of a nucleic acid sequence that is to be identified, amplified, or mutated and of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long.

The primer or probe may, for example without limitation, be prepared by direct chemical synthesis, by PCR (U.S. Pat. Nos. 4,683,195 and 4,683,202), or by excising the nucleic acid specific fragment from a larger nucleic acid molecule.

Transgenic Plants and Transformed Plant Host Cells

The invention is also directed to transgenic plants and transformed host cells which comprise, in a 5' to 3' orientation, a promoter operably linked to a heterologous structural nucleic acid sequence. Other nucleic acid sequences may also be introduced into the plant or host cell along with the promoter and structural nucleic acid sequence. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

Means for preparing such recombinant vectors are well known in the art. For example, methods for making recombinant vectors particularly suited to plant transformation are described in U.S. Pat. Nos. 4,971,908, 4,940,835, 4,769,061 and 4,757,011. These vectors have also been reviewed (Rodriguez et al., 1988; Glick et al., 1993).

Typical vectors useful for expression of nucleic acids in cells and higher plants are well known in the art and include vectors derived from the tumor-inducing (Ti) plasmid of *Agrobacterium tumefaciens* (Rogers et al., 1987). Other recombinant vectors useful for plant transformation, have also been described (Fromm et al., 1985). Elements of such recombinant vectors include, without limitation, discussed above.

A transformed host cell may generally be any cell which is compatible with the present invention. A transformed host plant or cell can be or derived from a monocotyledonous plant or a dicotyledonous plant including, but not limited to canola, crambe, maize, mustard, castor bean, sesame, cottonseed, linseed, soybean, *Arabidopsis, Phaseolus*, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris, Brassica napus*, turfgrass, sugarbeet, coffee and dioscorea (Christou, In: Particle Bombardment for Genetic Engineering of Plants, Biotechnology Intelligence Unit, Academic Press, San Diego, Calif. (1996)), with canola, maize, *Brassica campestris, Brassica napus*, rapeseed, soybean, safflower, wheat, rice and sunflower preferred, and canola, rapeseed, maize, *Brassica campestris, Brassica napus*, soybean, sunflower, safflower, oil palms, and peanut more preferred. In a particularly preferred embodiment, the plant or cell is or derived from canola. In another particularly preferred embodiment, the plant or cell is or derived from *Brassica napus*. In another particularly preferred embodiment, the plant or cell is or derived from soybean.

The soybean cell or plant is preferably an elite soybean cell line. An "elite line" is any line that has resulted from breeding and selection for superior agronomic performance. Examples of elite lines are lines that are commercially available to farmers or soybean breeders such as HARTZ™ variety H4994, HARTZ™ variety H5218, HARTZ™ variety H5350, HARTZ™ variety H5545, HARTZ™ variety H5050, HARTZ™ variety H5454, HARTZ™ variety H5233, HARTZ™ variety H5488, HARTZ™ variety HLA572, HARTZ™ variety H6200, HARTZ™ variety H6104, HARTZ™ variety H6255, HARTZ™ variety H6586, HARTZ™ variety H6191, HARTZ™ variety H7440, HARTZ™ variety H4452 Roundup Ready™, HARTZ™ variety H4994 Roundup Ready™, HARTZ™ variety H4988 Roundup Ready™, HARTZ™ variety H5000 Roundup Ready™, HARTZ™ variety H5147 Roundup Ready™, HARTZ™ variety H5247 Roundup Ready™, HARTZ™ variety H5350 Roundup Ready™, HARTZ™ variety H5545 Roundup Ready™, HARTZ™ variety H5855 Roundup Ready™, HARTZ™ variety H5088 Roundup Ready™, HARTZ™ variety H5164 Roundup Ready™, HARTZ™ variety H5361 Roundup Ready™, HARTZ™ variety H5566 Roundup Ready™, HARTZ™ variety H5181 Roundup Ready™, HARTZ™ variety H5889 Roundup Ready™, HARTZ™ variety H5999 Roundup Ready™, HARTZ™ variety H6013 Roundup Ready™, HARTZ™ variety H6255 Roundup Ready™, HARTZ™ variety H6454 Roundup Ready™, HARTZ™ variety H6686 Roundup Ready™, HARTZ™ variety H7152 Roundup Ready™, HARTZ™ variety H7550 Roundup Ready™, HARTZ™ variety H8001 Roundup Ready™ (HARTZ SEED, Stuttgart, Ark., U.S.A.); A0868, AGO901, A1553, A1900, AG1901, A1923, A2069, AG2101, AG2201, A2247, AG2301, A2304, A2396, AG2401, AG2501, A2506, A2553, AG2701, AG2702, A2704, A2833, A2869, AG2901, AG2902, AG3001, AG3002, A3204, A3237, A3244, AG3301, AG3302, A3404, A3469, AG3502, A3559, AG3601, AG3701, AG3704, AG3750, A3834, AG3901, A3904, A4045, AG4301, A4341, AG4401, AG4501, AG4601, AG4602, A4604, AG4702, AG4901, A4922, AG5401, A5547, AG5602, A5704, AG5801, AG5901, A5944, A5959, AG6101, QR4459 and QP4544 (Asgrow Seeds, Des Moines, Iowa, U.S.A.); DeKalb variety CX445 (DeKalb, Ill.).

The invention is also directed to a method of producing transformed plants which comprise, in a 5' to 3' orientation, a promoter operably linked to a heterologous structural nucleic acid sequence. Other sequences may also be introduced into plants along with the promoter and structural nucleic acid sequence. These other sequences may include 3' transcriptional terminators, 3' polyadenylation signals, other untranslated sequences, transit or targeting sequences, selectable markers, enhancers, and operators. Preferred recombinant vectors, structural nucleic acid sequences, promoters, and other regulatory elements including, without limitation, those described herein.

The method generally comprises the steps of selecting a suitable plant, transforming the plant with a recombinant vector, and obtaining the transformed host cell.

There are many methods for introducing nucleic acids into plants. Suitable methods include bacterial infection (e.g., Agrobacterium), binary bacterial artificial chromosome vectors, direct delivery of nucleic acids (e.g., via PEG-mediated transformation, desiccation/inhibition-mediated nucleic acid uptake, electroporation, agitation with silicon carbide fibers, and acceleration of nucleic acid coated particles, etc. (reviewed in Potrykus et al., 1991)).

Technology for introduction of nucleic acids into cells is well known to those of skill in the art. Methods can generally be classified into four categories: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253), and particle acceleration (Johnston and Tang, 1994; Fynan et al., 1993); (3) viral vectors (Clapp, 1993; Lu et al., 1993; Eglitis and Anderson, 1988); and (4) receptor-mediated mechanisms (Curiel et al., 1992; Wagner et al., 1992). Alternatively, nucleic acids can be directly introduced into pollen by directly injecting a plant's reproductive organs (Zhou et al., 1983; Hess, 1987; Luo et al., 1988; Pena et al., 1987). In another aspect nucleic acids may also be injected into immature embryos (Neuhaus et al., 1987).

Regeneration, development, and cultivation of plants from transformed plant protoplast or explants is taught in the art (Weissbach and Weissbach, 1988; Horsch et al., 1985). Transformants are generally cultured in the presence of a selective media which selects for the successfully transformed cells and induces the regeneration of plant shoots (Fraley et al., 1983). Such shoots are typically obtained within two to four months.

Shoots are then transferred to an appropriate root-inducing medium containing the selective agent and an antibiotic to prevent bacterial growth. Many of the shoots will develop roots. These are then transplanted to soil or other media to allow the continued development of roots. The method, as outlined, will generally vary depending on the particular plant employed.

Preferably, the regenerated transgenic plants are self-pollinated to provide homozygous transgenic plants.

Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

A transgenic plant may pass along the nucleic acid sequence encoding the enhanced gene expression to its progeny. The transgenic plant is preferably homozygous for the nucleic acid encoding the enhanced gene expression and transmits that sequence to all of its offspring upon as a result of sexual reproduction. Progeny may be grown from seeds produced by the transgenic plant. These additional plants may then be self-pollinated to generate a true breeding line of plants.

The progeny from these plants are evaluated, among other things, for gene expression. The gene expression may be detected by several common methods such as western blotting, northern blotting, immunoprecipitation, and ELISA.

Plants or agents of the present invention can be utilized in methods, for example without limitation, to obtain a seed that expresses a structural nucleic acid molecule in that seed, to obtain a seed enhanced in a product of a structural gene, to obtain meal enhanced in a product of a structural gene, to obtain feedstock enhanced in a product of a structural gene, and to obtain oil enhanced in a product of a structural gene.

Plants utilized in such methods may be processed. A plant or plant part may be separated or isolated from other plant parts. A preferred plant part for this purpose is a seed. It is understood that even after separation or isolation from other plant parts, the isolated or separated plant part may be contaminated with other plant parts. In a preferred aspect, the separated plant part is greater than about 50% (w/w) of the separated material, more preferably, greater than about 75% (w/w) of the separated material, and even more preferably greater than about 90% (w/w) of the separated material. Plants or plant parts of the present invention generated by such methods may be processed into products using known techniques. Preferred products are meal, feedstock and oil.

Feed, Meal, Protein and Oil Preparations

Any of the plants or parts thereof of the present invention may be processed to produce a feed, meal, protein or oil preparation. A particularly preferred plant part for this purpose is a seed. In a preferred embodiment the feed, meal, protein or oil preparation is designed for ruminant animals. Methods to produce feed, meal, protein and oil preparations are known in the art. See, for example, U.S. Pat. Nos. 4,957,748, 5,100,679, 5,219,596, 5,936,069, 6,005,076, 6,146,669 and 6,156,227. In a preferred embodiment, the protein preparation is a high protein preparation. Such a high protein preparation preferably has a protein content of greater than about 5% w/v, more preferably about 10% w/v, and even more preferably about 15% w/v. In a preferred oil preparation, the oil preparation is a high oil preparation with an oil content derived from a plant or part thereof of the present invention of greater than about 5% w/v, more preferably greater than about 10% w/v, and even more preferably greater than about 15% w/v. In a preferred embodiment the oil preparation is a liquid and of a volume greater than about 1, about 5, about 10 or about 50 liters. The present invention provides for oil produced from plants of the present invention or generated by a method of the present invention. Such oil may be a minor or major component of any resultant product. Moreover, such oil may be blended with other oils. In a preferred embodiment, the oil produced from plants of the present invention or generated by a method of the present invention constitutes greater than about 0.5, about 1, about 5, about 10, about 25, about 50, about 75 or about 90% by volume or weight of the oil component of any product. In another embodiment, the oil preparation may be blended and can constitute greater than about 10, about 25, about 35, about 50 or about 75% of the blend by volume. Oil produced from a plant of the present invention can be admixed with one or more organic solvents or petroleum distillates.

Seed Containers

Seeds of the plants may be placed in a container. As used herein, a container is any object capable of holding such seeds. A container preferably contains greater than about 500, about 1,000, about 5,000, or about 25,000 seeds where at least about 10, about 25, about 50, about 75 or about 100% of the seeds are derived from a plant of the present invention.

Breeding Programs

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g., Fehr, *Principles of Cultivar Development* Vol. 1, pp. 2–3 (1987)).

A transgenic plant of the present invention may also be reproduced using apomixis. Apomixis is a genetically controlled method of reproduction in plants where the embryo is formed without union of an egg and a sperm. There are three basic types of apomictic reproduction: (1) apospory where the embryo develops from a chromosomally unreduced egg in an embryo sac derived from the nucleus, (2) diplospory where the embryo develops from an unreduced egg in an embryo sac derived from the megaspore mother cell, and (3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636.

Other Organisms

A nucleic acid of the present invention may be introduced into any cell or organism such as a mammalian cell, mammal, fish cell, fish, bird cell, bird, algae cell, algae, fungal cell, fungi, or bacterial cell. Preferred host and transformants include: fungal cells such as Aspergillus, yeasts, mammals, particularly bovine and porcine, insects, bacteria, and algae. Preferred bacteria are *E. coli* and *Agrobacterium tumefaciens*.

Methods to transform such cells or organisms are known in the art (EP 0 238 023; Yelton et al., 1984; Malardier et al., 1989; Becker and Guarente; Ito et al., 1983; Hinnen et al., 1978; and Bennett and LaSure, 1991). Methods to produce proteins from such organisms are also known (Kudla et al., 1990; Jarai and Buxton, 1994; Verdier, 1990; MacKenzie et al., 1993; Hartl et al., 1994; Bergeron et al., 1994; Demolder et al., 1994; Craig, 1993; Gething and Sambrook, 1992; Puig and Gilbert, 1994; Wang and Tsou, 1993; Robinson et al., 1994; Enderlin and Ogrydziak, 1994; Fuller et al., 1989; Julius et al., 1984; and Julius et al., 1983).

EXAMPLES

The following examples are provided and should not be interpreted in any way to limit the scope of the present invention.

Example 1

Generation of Clones of a 7Sα Promoter from Soybean (*Glycine max* L.)

A 7Sα promoter is obtained from soybean genomic DNA (Asgrow A3244) using a Universal Genome Walker Kit (Clontech Laboratories, Inc., Palo Alto, Calif.) and following manufacturer's specifications. The procedure consists of two PCR amplifications, using an adapter primer and a gene-specific primer for each amplification reaction. To identify a region of minimal homology that would be suitable as template DNA, the sequences of the coding regions of the 7Sα and 7Sα' (GlcX (7Sα') and GlcA (7Sα)) genes are aligned and two regions of non-homology are identified (FIG. 1). Based upon the identified regions of non-homology, the following gene specific primers are prepared:

For the primary PCR amplification, GlcA-GW-primary: 3' end (complementary to the underlined sequence in FIG. 1) 5'-CTTCTGATGAGGTGGGCGTGGGAATGGGAA-3' [SEQ ID NO: 6]

For the secondary PCR amplification, GlcA-GW-nested (with cloning sites BglII and NcoI added at the 5' end of the primer): 3' end (complementary to the bold sequence in FIG. 1) 5'-CCATGGAGATCTATCTTGTTCTCATCCTCATCC TCATC-3' [SEQ ID NO: 7]

The following adapter primer is used in this methodology:

```
5' end Primary: AP1 seq:
                                    [SEQ ID NO:9]
5'-GTATACGACTCACTATAGGGC-3'

AP5 (with cloning sites HindIII and
PstI added at the 5' end of the primer)
Nested 5' end
                                    [SEQ ID NO:5]
5'-AAGCTTCTGCAGGGTCGACGGCCCGGGCTGGT-3'
```

From this procedure, three clones are isolated and sequenced. A sequence alignment illustrated that all three clones represent the same 7Sα gene with clone 8A as the longest. Clones are identified as 8A (2.3 Kb in length), 7C (1.5 Kb in length) and 9C (1.3 Kb in length). These initial clones contain the sequence associated with both the promoter and a portion of the coding region of a 7Sα gene (one of the subunits of β-conglycinin). To confirm that the clone is a 7Sα gene, the 3' sequence of the 8A clone is aligned with a published cDNA sequence (GenBank Accession Number X17698). Such an alignment confirms that the PCR product is homologous to the upstream region of the 7Sα and not the 7Sα' gene.

Clones 7C, 8A, and 9C are then subcloned to provide smaller fragments containing only the promoter and the 5' UTR regions of the 7Sα gene. PCR amplification reactions as described above are performed using the clones 7C, 8A, and 9C as the templates. The AP5 primer is the adapter primer, and the gene specific primer is: 5'-CCATGGAGA TCTAAGGAGGTTGCAACGAGCGTGGCAT-3' [SEQ ID NO: 10]

This gene specific primer is designed to introduce a BglII and NcoI restriction site at the 3' end to facilitate subsequent cloning. Resulting clones are sequenced using standard methodology and subcloned into a new pGEM-T easy vector (Promega, Madison, Wis., U.S.; U.S. Pat. No. 4,766,072) generating the following:

p-GEM-T 1A. 1.7 Kb insert derived from the original clone 8A,
p-GEM-T 2A. 1.3 Kb insert derived from the original clone 7C, and
p-GEM-T 3A. 1.1 Kb insert derived from the original clone 9C.

Nucleotide sequences of p-GEM-T 1A, p-GEM-T 2A, and p-GEM-T 3A are used to predict the corresponding amino acid sequences. Predicted amino acid sequences are then aligned to the protein translation sequence of the 7Sα gene product (GlcA) (GenBank Accession Number X17698 and SWISS-PROT Accession Number P13916) to identify a start codon. Sequences are aligned using the GCG software (Genetics Computer Group, Oxford Molecular Group, Inc.) sequence alignment function. The 1A, 2A, and 3A clones are then used as templates for another PCR reaction using the AP5 as the adapter primer and the following sequence as the gene specific primer: 5'-CCATGGAGATCTAGTA TCTTAATTATTTATTAAGGTAT-3' [SEQ ID NO: 8]

Additionally, NcoI and BglII sites are added at the 5' end of the primer (shown in italics). The PCR products of this reaction are purified and cloned again into pGEM-T easy vector resulting in: p-GEM-T 1T, 1724 base pair insert derived from the clone 1A; p-GEM-T "new" 2A, 1135 base pair insert derived from the clone 2A; and p-GEM-T "new" 3A, 918 base pair insert derived from the clone 3A. The sequence of p-GEM-T 1T is shown in FIG. 2.

Example 2

This example demonstrates that the promoter activities of the new cloned 7Sα variants are confirmed in transiently transformed soybean cotyledons.

The three clones from example 1 (1T, new 2A, and new 3A) are purified by gel electrophoresis (QIAquick kit, Cat. No. 28704, Qiagen Company, Valencia, Calif.) and subcloned into pMON8677 (FIG. 3), in the position originally occupied by the e35S promoter, up stream of the GUS reporter gene. The resulting plasmid maps are shown in FIG. 2a as pMON55548 (1T), FIG. 3a as pMON55546 (new 2A) and FIG. 4 as pMON55547 (new 3A). Two of these plasmids, pMON55546 and pMON55548, are used in the transient assays of soybean cotyledons.

Seeds from soybean plants (Asgrow A3244) are harvested 25–28 days after flowering and osmotically treated overnight at 25° C. in dark on GAMBORG's medium (G5893, Sigma Company, St. Louis, Mo.) supplemented with of 50 mM glutamine, 111 mM maltose, 125 mM raffinose, 125 mM mannitol and 3g/l purified agar, pH 5.6. The resulting 125 cotyledons are cut in half and bombarded with purified supercoiled DNA of the 7Sα promoter constructs from pMON55546 and pMON55548 using particle gun technology (Maliga et al., 1995, "Methods in Plant Molecular Biology, A Laboratory Course Manual," Cold Spring Harbor Laboratory Press, page 47). A separate e35S driven luciferase construct is included in a 1:1 molar ratio with each of the promoter constructs as a low expression control. Bombarded tissues are then incubated for 48 hours at 25° C.

Proteins are extracted from six bombarded soybean cotyledons using 1 ml extraction buffer containing 0.1 M potassium phosphate (pH 7.8), 10 mM DTT, 1 mM EDTA, 5% glycerol, and proteinase inhibitor (1 tablet/50 ml, Roche Molecular Biochemicals, Indianapolis, Ind.). A 100 μl aliquot of the protein extract is used for Luciferase assay following a "Steady-Glo" procedure by Promega (Cat. No. E25 10, Promega Corporation Madison, Wis.). A 50 μl aliquot of the protein extract is used for a standard GUS assay protocol with minor modifications (Maliga et al., 1995, "Methods in Plant Molecular Biology, A Laboratory Course Manual", Cold Spring Harbor Laboratory Press, page 29). Each sample is assayed twice and the average value is used for data analysis. GUS activity is normalized using luciferase activity and the results indicate that all variants of 7Sα promoters are functional in soybean cotyledon tissues.

Example 3

Production of Transgenic Soybean Plants Containing the 7Sα Promoter

The expression cassette in pMON55548 (7Sα-1T-GUS-NOS-3') was subcloned to generate vector pMON55554, an agrobacterium transformation vector capable of demonstrating the effectiveness of a 7Sα promoter in soybean plants (FIG. 5). A glyphosate-resistant selection marker (CP4) is also included in pMON55554. The vector is introduced into an ABI *Agrobacterium tumefaciens* bacterial strain and the resulting transformed cells are used to infect cotyledons of soybean (Asgrow A3244). As a control, a truncated Arcelin 5 promoter is used in place of the 7Sα-1T to generate pMON55542 (FIG. 6). The vector is introduced into an ABI *Agrobacterium tumefaciens* bacterial strain and the resulting transformed cells are used to infect cotyledons of soybean (Asgrow A3244).

Glyphosate resistant plants are selected after regeneration of plants from the tissues infected by the *A. tumefaciens*. Mature seeds from the selected plants are analyzed for GUS activity. To assay for GUS activity, eight seeds from each transgenic event (line) are ground individually. About 20 mg ground seed tissue is extracted using 200 μl extraction buffer containing 0.1 M potassium phosphate (pH 7.8), 10 mM DTT, 1 mM EDTA, 5% glycerol, and proteinase inhibitor (1 tablet/50 ml, Roche Molecular Biochemicals, Indianapolis, Ind.). The protein content of the extract is determined using Bio-Rad Protein Assay (Bio-Rad, #61234A) and the GUS activity is measured using a standard GUS assay protocol with minor modifications (Maliga et al., 1995, "Methods in Plant Molecular Biology, A Laboratory Course Manual", Cold Spring Harbor Laboratory Press, page 29). The GUS activity is normalized against the protein concentration. Each sample was assayed twice and the average value was used for data analysis.

An event (line) is rejected if none of the eight seeds had detectable GUS activity. Among each of the events showing GUS activity, the seed having the highest activity is selected. GUS activity assay is repeated for the selected seeds and the results are summarized in FIG. 7. The comparison between 28 positive events of pMON55554 and 11 positive events of pMON55542 shows that the 7Sα promoter is, at a minimum, as strong as the truncated Arcelin 5 promoter (FIG. 7).

Example 4
Production of Transgenic Arabidopsis Containing the 7Sα Promoter or Arcelin 5 Promoter Expression of GUS driven by either the 7Sα1T promoter in pMON55553 (FIG. 8) or the tArc5 in pMON55541 (FIG. 9) is examined in *Arabidopsis thaliana*. Expression of pMON55553 (7Sα1T-GUS-NOS) GUS and pMON55541 (tArc5-GUS-NOS) GUS is examined in a one week-old seedling and in a mature plant. Plants and seedlings expressing the pMON55553 plasmid show that GUS is absent in roots or mature leaves when the 7Sα1T promoter is used. Activity is seen in hypocotyls and cotyledons, which is caused by the residual GUS protein synthesized during embryogenesis. Plants and seedlings expressing pMON55541 show that GUS is present in roots and mature leaves in addition to the signals detected in hypocotyls and cotyledons when the tArc5 promoter is used. The data illustrates that 7Sα promoter has improved seed-specificity compared to the tArc5 promoter.

References

Ainley et al., *Plant Mol. Biol.*, 14:949, 1990.
Ausubel et al., *Current Protocols in Molecular Biology*, John Wiley and Sons, Inc., 1995.
Bartley and Scolnik, *Plant Physiol.*, 104:1469–1470, 1994.
Back et al., *Plant Mol. Biol.*, 17:9, 1991.
Bauer et al., *Gene*, 37:73, 1985.
Becker and Guarente, In: Abelson and Simon (eds.), *Guide to Yeast Genetics and Molecular Biology, Methods Enzymol.*, Vol. 194, pp. 182–187, Academic Press, Inc., New York.
Bennett and LaSure (eds.), *More Gene Manipulations in Fungi*, Academic Press, CA, 1991.
Bergeron et al., *TIBS*, 19:124–128, 1994.
Bustos et al., *EMBO J.*, 10: 1469–1479, 1991.
Castresana et al., *EMBO J.*, 7:1929–1936, 1988.
Capecchi, *Cell*, 22(2):479–488, 1980.
Cerda-Olmedo et al., *J. Mol. Biol.*, 33:705–719, 1968.
Chau et al., *Science*, 244:174–181. 1989.
Christensen et al., *Plant Mol. Biol.*, 18:675,689, 1992.
Clapp, *Clin. Perinatol.*, 20(1):155–168, 1993.
Costa et al. *Methods Mol. Biol.*, 57:31–44, 1996.
Craik, *BioTechniques*, 3:12–19, 1985.
Craig, *Science*, 260:1902–1903, 1993.
Curiel et al., *Hum. Gen. Ther.*, 3(2):147–154, 1992.
Cyanobase, http://www.kazusa.or.jp/cyanobase.
Dellaporta et al., *Stadler Symposium*, 11:263–282, 1988.
Demolder et al., *J. Biotechnology*, 32:179–189, 1994.
Deng and Nickloff, *Anal. Biochem.*, 200:81, 1992.
D'Halluin et al., *Bio/Technology* 10: 309–314, 1992.
Doyle et al., *J. Biol. Chem.*, 261:9228–9238, 1986.
Eglitis and Anderson, *Biotechniques*, 6(7):608–614, 1988.
Enderlin and Ogrydziak, *Yeast*, 10:67–79, 1994.
Feinbaum et al., *Mol. Gen. Genet.*, 226:449–456, 1991.
Fraley et al., *Proc. Natl. Acad. Sci. U.S.A.*, 80:4803, 1983.
Frits Eckstein et al., *Nucleic Acids Research*, 10:6487–6497, 1982.
Fromm et al., *Proc. Natl. Acad. Sci. USA*, 82(17): 5824–5828, 1985.
Fromm et al., *Bio/Technology*, 8:833, 1990.
Fuller et al., *Proc. Natl. Acad. Sci. (U.S.A.)*, 86:1434–1438, 1989.
Fynan et al., *Proc. Natl. Acad. Sci. USA*, 90(24): 11478–11482, 1993.
Gething and Sambrook, *Nature*, 355:33–45, 1992.
Glick et al., *Methods in Plant Molecular Biology and Biotechnology*, CRC Press, Boca Raton, Fla., 1993.
Graham and Van der Eb, *Virology*, 54(2):536–539, 1973.
Greener et al., *Mol. Biotechnol.*, 7:189–195, 1997.
Hartl et al., *TIBS*, 19:20–25, 1994.
Hershey and Stoner, *Plant Mol. Biol.*, 17:679–690, 1991.
Hess, *Intern Rev. Cytol.*, 107:367, 1987.
Hinchee et al., *Bio/Technology*, 6:915–922, 1988.
Hinnen et al., *Proc. Natl. Acad. Sci. (U.S.A.)*, 75:1920, 1978.
Horsch et al., *Science*, 227:1229–1231, 1985.
Ikatu et al., *Bio/Technol.*, 8:241–242, 1990.
Jarai and Buxton, *Current Genetics*, 26:2238–2244, 1994.
Jefferson (I), *Plant Mol. Biol, Rep.*, 5:387–405, 1987.
Jefferson (II) et al., *EMBO J.*, 6:3901–3907, 1987.
Johnston and Tang, *Methods Cell Biol.*, 43(A):353–365, 1994.
Jones et al., *Science*, 266:789–793, 1994.
Jones et al., *Mol. Gen. Genet.*, 1987.
Julius et al., *Cell*, 32:839–852, 1983.
Julius et al., *Cell*, 37:1075–10–89, 1984.
Kares et al., *Plant Mol. Biol.*, 15:905, 1990.
Katz et al., *J. Gen. Microbiol.*, 129:2703–2714, 1983.
Keegstra, *Cell*, 56(2):247–253, 1989.
Keller et al., *EMBO L.*, 8:1309–1314, 1989.
Knutzon et al., *Proc. Natl. Acad. Sci U.S.A.*, 89:2624–2628, 1992.
Kridl et al., *Seed Sci. Res.*, 1:209, 1991.
Kudla et al., *EMBO*, 9:1355–1364, 1990.
Kuhlemeier et al., *Seeds*, 1:471, 1989.

Kunkel, *Proc. Natl. Acad. Sci. U.S.A.,* 82:488–492, 1985.
Kyte and Doolittle, *J. Mol. Biol.,* 157:105–132, 1982.
Lam and Chua, *J. Biol. Chem.,* 266:17131–17135, 1990.
Lam and Chua, *Science,* 248:471, 1991.
Lipman and Pearson, *Science,* 227:1435–1441, 1985.
Lindstrom et al., *Developmental Genetics,* 11: 160, 1990.
Lois et al., *Proc. Natl. Acad. Sci. U.S.A.,* 95(5):2105–2110, 1998.
Lu et al., *J. Exp. Med.,* 178(6):2089–2096, 1993.
Luo et al., *Plant Mol. Biol. Reporter,* 6:165, 1988.
MacKenzie et al., *Journal of Gen. Microbiol.,* 139:2295–2307, 1993.
Malardier et al., *Gene,* 78:147–156, 1989.
Mandel et al., *Plant Mol. Biol,* 29:995–1004, 1995.
McElroy et al., *Seeds,* 2:163–171, 1990.
Nawrath et al., *Proc. Natl. Acad. Sci. U.S.A.,* 91:12760–12764, 1994.
Needleman and Wunsch, *Journal of Molecular Biology,* 48:443–453, 1970.
Neuhaus et al., *Theor. Appl. Genet.,* 75:30, 1987.
Odell et al., *Nature,* 313:810, 1985.
Osuna et al., *Critical Reviews In Microbiology,* 20:107–116, 1994.
Ou-Lee et al., *Proc. Natl. Acad. Sci U.S.A.,* 83:6815, 1986.
Ow et al., *Science,* 234:856–859, 1986.
Pearson and Lipman, *Proc. Natl. Acad. Sci. (U.S.A.),* 85:2444–2448, 1988.
Pearson, "Rapid and Sensitive Sequence Comparison with FASTP and FASTA." In *Methods in Enzymology,* (R. Doolittle, ed.), 183, 63–98, Academic Press, San Diego, Calif., USA, 1990.
Pearson, *Protein Science,* 4:1145–1160, 1995.
Pena et al., *Nature,* 325:274, 1987.
Poszkowski et al., *EMBO J.,* 3:2719, 1989.
Potrykus et al., *Ann. Rev. Plant Physiol. Plant Mol. Biol.,* 42:205, 1991.
Potrykus et al., *Mol. Gen. Genet.* 199:183–188, 1985.
Puig and Gilbert, *J. Biol. Chem.,* 269:7764–7771, 1994.
Pyee et al., *Plant J.,* 7:49–59, 1995.
Reynaerts et al., "Selectable and Screenable Markers." In *Plant Molecular Biology Manual,* (Gelvin and Schilperoort, eds.), Kluwer, Dordrecht, 1988.
Richins et al., *Nucleic Acids Res.,* 20:8451, 1987.
Robinson et al., *Bio/Technology,* 1:381–384, 1994.
Rodriguez et al., Vectors: A Survey of Molecular Cloning Vectors and Their Uses, Butterworths, Boston, 1988.
Rogan and Bessman, *J. Bacteriol.,* 103:622–633, 1970.
Rogers et al., *Meth. In Enzymol,* 153:253–277, 1987.
Saint Guily et al., *Plant Physiol.,* 100(2):1069–1071, 1992.
Samac et al., *Seeds,* 3:1063–1072, 1991.
Sambrook et al., *Molecular Cloning: A Laboratory Manual,* Second Edition, Cold Spring Harbor Laboratory Press, Cold Spring Harbor, N.Y., 1989.
Sato et al., *J. DNA Res.,* 7(1):31–63, 2000.
Schulze-Lefert et al., *EMBO J.,* 8:651, 1989.
Simpson, *Science,* 233:34, 1986.
Singer and Kusmierek, *Ann. Rev. Biochem.,* 52:655–693, 1982.
Slighton and Beachy, *Planta,* 172:356, 1987.
Smith et al., In *Genetic Engineering: Principles and Methods,* (Setlow et al., ed.), Plenum Press, NY, 1–32, 1981.
Smith and Waterman, *Advances in Applied Mathematics,* 2:482–489, 1981.
Smith et al., *Nucleic Acids Research,* 11:2205–2220, 1983.
Smith et al., *Plant J.,* 11:83–92, 1997.
Stalker et al., *J. Biol. Chem.,* 263:6310–6314, 1988.
Sutcliffe et al., *Proc. Natl. Acad. Sci. (U.S.A.),* 75:3737–3741, 1978.
Takahashi et al., *Proc. Natl. Acad. Sci. U.S.A.,* 951(17):9879–9884, 1998.
Thillet et al., *J. Biol. Chem.,* 263:12500–12508, 1988.
Vandeyar et al., *Gene,* 65:129–133, 1988
Van Tunen et al., *EMBO J.,* 7:1257, 1988.
Verdier, *Yeast,* 6:271–297, 1990.
Vodkin et al., *Cell,* 34:1023, 1983.
Vogel et al., *J. Cell Biochem., (Suppl)* 13D:312, 1989.
Wagner et al., *Proc. Natl. Acad. Sci. USA,* 89(13): 6099–6103, 1992.
Wang and Tsou, *FASEB Journal,* 7:1515–1517, 1993.
Weissbach and Weissbach, *Methods for Plant Molecular Biology,* (Eds.), Academic Press, Inc., San Diego, Calif., 1988.
Weisshaar et al., *EMBO J.,* 10:1777–1786, 1991.
Wenzler et al., *Plant Mol. Biol.,* 12:41–50, 1989.
Williams et al., *Biotechnology,* 10:540–543, 1992.
Wong and Neumann, *Biochim. Biophys. Res. Commun.,* 107(2):584–587, 1982.
Xia et al., *J. Gen. Microbiol.,* 138:1309–1316, 1992.
Yang et al., *Proc. Natl. Acad. Sci. USA,* 87:4144–48, 1990.
Yamaguchi-Shinozaki et al., *Plant Mol. Biol.,* 15:905, 1990.
Yelton et al., *Proc. Natl. Acad. Sci. (U.S.A.),* 81:1470–1474, 1984.
Zhou et al., *Methods in Enzymology,* 101:433, 1983.
Zukowsky et al., *Proc. Natl. Acad. Sci. (U.S.A.),* 80:1101–1105, 1983.
U.S. Pat. Nos. 4,683,195; 4,683,202; 4,757,011; 4,769,061; 4,885,357; 4,886,878; 4,940,835; 4,957,748; 4,971,908; 5,057,419; 5,093,249; 5,100,679; 5,147,792; 5,215,912; 5,219,596; 5,270,200; 5,298,421; 5,304,481; 5,344,771; 5,362,865; 5,576,203; 5,508,468; 5,003,045; 5,955,329; 5,367,110; 5,858,749; 6,040,160; 5,610,041; 5,618,988; 6,107,060; 5,811,636; 4,766,072; 5,003,045; 5,576,203; 5,384,253; 5,443,974; 5,512,482; 5,530,186; 5,534,421; 5,552,306; 5,589,616; 5,508,468; 5,614,393; 5,663,068; 5,663,068; 5,633,436; 5,639,790; 5,654,402; 5,659,645; 5,689,050; 5,689,050; 5,689,052; 5,705,391; 5,760,206; 5,759,829; 5,789,220; 5,807,893; 5,850,024; 5,856,157; 5,866,789; 5,885,802; 5,885,801; 5,914,450; 5,942,660; 5,945,585; 5,952,544; 5,955,650; 5,965,727; 5,995,329; 5,990,384; 5,990,389; 5,936,069; 5,939,599; 6,005,076; 6,051,754; 6,075,183; 6,043,411; 6,100,091; 6,107,051; 6,110,891; 6,117,677; 6,194,167; 6,146,669; 6,147,279; 6,156,227; 6,172,106; 6,232,122.
European Applications 0 154 204; 0 238 023; 0 255 378.
PCT Applications: WO 90/01869; WO 91/13993; WO 92/14822; WO 93/08682; WO 94/20628; WO 95/19442; WO 97/26366; WO 97/28247; WO 97/22703; WO 98/55601; WO 98/26064; WO 96/17064; WO 97/35023; WO 00/19839; WO 99/06581; WO 99/02656; WO 99/40209; WO 99/11800; WO 99/49058; WO 00/32757; WO 00/10380.

55

What is claimed is:

1. A transformed plant containing a nucleic acid molecule that comprises an isolated promoter selected from the group consisting of SEQ ID NO: 12, SEQ ID NO: 13 and SEQ ID NO: 14.

2. The transformed plant of claim 1, wherein said promoter is operably linked to a structural nucleic acid sequence.

3. The transformed plant of claim 2, wherein said structural nucleic acid sequence encodes a protein selected from the group consisting of zeins, 7S protein, brazil nut protein, phenylalanine free protein, β-conglycinin, 11S protein, alpha-hordothionin, arcelin seed storage protein, lectin, and glutenin.

4. The transformed plant of claim 2, wherein said structural nucleic acid sequence encodes a protein selected from the group consisting of a tyrA, slr1 736, ATPT2, dxs, dxr, GGPPS, HPPD, GMT, MT1, AANT1, slr 1737, and a homogentisic acid dioxygenase.

5. The transformed plant of claim 2, wherein said structural nucleic acid sequence encodes a protein selected from the group consisting of anthranilate synthase, tryptophan decarboxylase, threonine deaminase, dihydrodipicolinate synthase, lysine ketoglutarate reductase and aspartate kinase.

6. The transformed plant of claim 2, wherein said structural nucleic acid sequence is oriented in a manner to suppress expression of a substantially homologous nucleic acid sequence that is endogenous to the transformed plant.

7. The transformed plant of claim 6, wherein said structural nucleic acid sequence is oriented to express an antisense RNA molecule.

8. The transformed plant of claim 1, wherein the transformed plant is selected from the group consisting of canola, crambe, mustard, castor bean, sesame, cottonseed, linseed, maize, soybean, *Arabidopsis, Phaseolus*, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris, Brassica napus*, turfgrass, sugarbeet, coffee and dioscorea.

9. The transformed plant of claim 8, wherein the transformed plant is soybean.

10. The transformed plant of claim 2, wherein said nucleic acid sequence is expressed in a seed.

11. A method of transforming a plant comprising: providing a nucleic acid molecule that comprises in the 5' to 3' direction an isolated promoter having a nucleic acid sequence selected from the group consisting of SEQ ID NO: 12, SEQ ID NO: 13, and SEQ ID NO: 14, operably linked to a structural nucleic acid sequence; and transforming a plant with the nucleic acid molecule.

12. The method of claim 11, further comprising growing said transformed plant such that it produces seed, wherein said nucleic acid molecule is transcribed in said seed; and harvesting said seed from said transformed plant.

13. A substantially purified nucleic acid molecule comprising an isolated promoter selected from the group consisting of SEQ ID NO: 12, SEQ ID NO: 13, and SEQ ID NO: 14.

14. A vector comprising the substantially purified nucleic acid molecule of claim 13.

15. A cell comprising the vector of claim 14.

16. The cell according to claim 15, wherein said cell is selected from the group consisting of a bacterial cell, an insect cell, a plant cell and a fungal cell.

17. The cell according to claim 16, wherein said bacterial cell is *Agrobacterium tumefaciens* or *E. coli*.

18. The cell according to claim 16, wherein said plant cell is a soybean cell.

* * * * *